(12) United States Patent
Gehlsen et al.

(10) Patent No.: US 10,113,164 B2
(45) Date of Patent: *Oct. 30, 2018

(54) PICHIA PASTORIS SURFACE DISPLAY SYSTEM

(71) Applicant: RESEARCH CORPORATION TECHNOLOGIES, INC., Tucson, AZ (US)

(72) Inventors: Kurt R. Gehlsen, Tucson, AZ (US); Thomas G. Chappell, San Marcos, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/107,234

(22) PCT Filed: Dec. 16, 2014

(86) PCT No.: PCT/US2014/070469
§ 371 (c)(1),
(2) Date: Jun. 22, 2016

(87) PCT Pub. No.: WO2015/100058
PCT Pub. Date: Jul. 2, 2015

(65) Prior Publication Data
US 2017/0002346 A1    Jan. 5, 2017

Related U.S. Application Data

(60) Provisional application No. 61/920,182, filed on Dec. 23, 2013.

(51) Int. Cl.
C12N 15/10    (2006.01)
C07K 14/39    (2006.01)
(Continued)

(52) U.S. Cl.
CPC .......... *C12N 15/1037* (2013.01); *C07K 14/39* (2013.01); *C12N 9/1051* (2013.01);
(Continued)

(58) Field of Classification Search
CPC .................................................. C12N 15/1037
See application file for complete search history.

(56) References Cited

U.S. PATENT DOCUMENTS 6,300,065 B1    10/2001   Kieke et al.
6,423,538 B1    7/2002   Wittrup et al.
(Continued)

FOREIGN PATENT DOCUMENTS

AU    2012227297 A1    10/2012
WO    WO 99/011904 A1    3/1999
(Continued)

OTHER PUBLICATIONS

Deschutter K. et al., "Pichia Surface Display: A Tool for Screening Single Domain Antibodies", Methods in Molecular Biology 911:125-134.

Jacobs P.P. et al., "Engineering Complex-Type N-Glycosylation in Pichia Pastoris Using GlycoSwitch Technology", Nature Protocols 4(1):58-70 (2009).

(Continued)

*Primary Examiner* — Jana A Hines
*Assistant Examiner* — Khatol S Shahnan Shah
(74) *Attorney, Agent, or Firm* — Scully, Scott, Murphy & Presser, P.C.

(57) ABSTRACT

This disclosure relates to novel *Pichia pastoris* display systems, e.g., display systems featuring the *Pichia pastoris* strains (such as SuperMan5) with substantially homogeneous N-glycans displayed on cell surface proteins.

12 Claims, 10 Drawing Sheets

Specification includes a Sequence Listing.

(51) Int. Cl.
*C12N 9/10* (2006.01)
*C12N 9/24* (2006.01)

(52) U.S. Cl.
CPC .... *C12N 9/2477* (2013.01); *C12Y 204/01232* (2013.01); *C12Y 302/01113* (2013.01)

(56) References Cited

U.S. PATENT DOCUMENTS

| | | | |
|---|---|---|---|
| 6,696,251 | B1 | 2/2004 | Wittrup et al. |
| 6,699,658 | B1 | 3/2004 | Wittrup et al. |
| 6,759,243 | B2 | 7/2004 | Kranz et al. |
| 7,465,787 | B2 | 12/2008 | Wittrup et al. |
| 7,569,357 | B2 | 8/2009 | Kranz et al. |
| 7,741,075 | B2 | 6/2010 | Inan |
| 8,067,339 | B2 | 11/2011 | Prinz et al. |
| 8,877,686 | B2 | 11/2014 | Zha et al. |
| 2005/0106664 | A1* | 5/2005 | Contreras ............ C12P 21/005 435/69.1 |
| 2009/0275137 | A1 | 11/2009 | Kranz et al. |
| 2009/0280560 | A1 | 11/2009 | Wittrup et al. |
| 2011/0021378 | A1 | 1/2011 | Callewaert et al. |
| 2011/0027831 | A1* | 2/2011 | Hamilton ......... C12Y 302/0101 435/84 |
| 2011/0275535 | A1 | 11/2011 | Loew |
| 2013/0018177 | A1 | 1/2013 | Hamilton |
| 2015/0211000 | A1 | 7/2015 | Zha et al. |
| 2015/0267212 | A1 | 9/2015 | Gehlsen et al. |

FOREIGN PATENT DOCUMENTS

| | | | |
|---|---|---|---|
| WO | WO 2004/003194 A2 | 1/2004 | |
| WO | WO 2007/127538 A1 | 11/2007 | |
| WO | 2009/111183 A1 | 9/2009 | |
| WO | 2010/005863 A1 | 1/2010 | |
| WO | WO 2013/043582 A1 | 3/2013 | |
| WO | WO 2013/135728 A1 | 9/2013 | |
| WO | 2014/066479 A1 | 5/2014 | |
| WO | WO 2014/066479 A1 | 5/2014 | |

OTHER PUBLICATIONS

Li W. et al., "Cell Surface Display and Characterization of Rhizopus Oryzae Lipase in Pichia Pastoris Using Sed1p as an Anchor Protein", Curr Microbiol 71:150-155 (2015).

Rhiel L. et al., "REAL-Select: Full-Length Antibody Display and Library Screening by Surface Capture on Yeast Cells", PLOS One 9(12):e114887 (19 pages) (Dec. 12, 2014).

Ryckaert S. et al., "Isolation of Antigen-Binding Camelid Heavy Chain Antibody Fragments (Nanobodies) from an Immune Library Displayed on the Surface of Pichia Pastoris", Journal of Biotechnology 145:93-98 (2010).

Ryckaert S. et al., "Fishing for Lectins from Diverse Sequence Libraries by Yeast Surface Display—An Exploratory Study", Glycobiology 18(2):137-144 (2008).

Shaheen H.H. et al., "A Dual-Mode Surface Display System for the Maturation and Production of Monoclonal Antibodies in Glyco-Engineered Pichia Pastoris", PLOS One 8(7):e70190 (10 pages) (Jul. 2013).

Zhao H. et al., "Interaction of a-Agglutinin and a-Agglutinin, *Saccharomyces cerevisia* Sexual Cell Adhesion Molecules", Journal of Bacteriology 183(9):2874-2880 (May 2001).

Adimab Announces 50th Therapeutic Program Under Its Funded Discovery Partnerships, Announces New commercial Licenses Exercised by Arsanis, Merrimack, and Mersana Therapeutics (3 pages) (Jun. 20, 2014).

International Search Report dated Apr. 3, 2015 issued in PCT/US2014/070469.

Krainer et al., "Recombinant protein expression in Pichia pastoris strains with an engineered methanol utilization pathway", Microbial Cell Factories (Feb. 13, 2012), vol. 11, No. 22, pp. 1-14.

Chiba, Yasunori et al., "Production of Human Compatible High Mannose-type (Man5GlcNAc2) Sugar Chains in *Saccharomyces cerevisiae*", The Journal of Biological Chemistry (Oct. 9, 1998), vol. 273, No. 41, pp. 26298-26304.

Daly, Rachel et al. "Expression of heterologous proteins in Pichia pastoris: a useful experimental tool in protein engineering and production", Journal of Molecular Recognition (Mar. 2005), vol. 18, No. 2, pp. 119-138.

* cited by examiner

FIG. 1

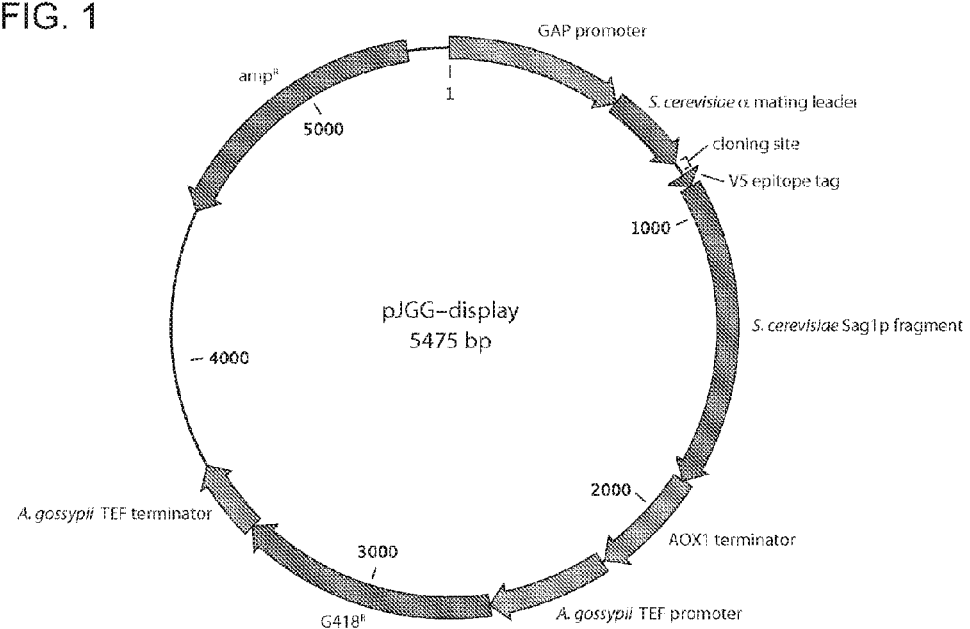

| LOCATION | FEATURE | ORIGIN |
|---|---|---|
| 1..558 | Eukaryotic Promoter | *Pichia pastoris* GAP promoter |
| 559..825 | Open Reading Frame | *S. cerevisiae* α mating factor leader |
| 826..867 | Cloning Site | *Bsa* I – *Xho* I – *Not* I – *Bsa* I |
| 868..909 | Open Reading Frame | V5 epitope tag |
| 910..1872 | Open Reading Frame | *S. cerevisiae* SAG1 gene fragment |
| 1873..2222 | Eukaryotic Terminator | *Pichia pastoris* AOX1 terminator |
| 2234..2612 | Eukaryotic Promoter | *Ashbya gossypii* TEF promoter |
| 2613..3422 | Open Reading Frame | G418 resistance protein |
| 3423..3659 | Eukaryotic Terminator | *Ashbya gossypii* TEF terminator |
| complement 4482..5342 | Open Reading Frame | Ampicillin resistance protein |

FIG. 2

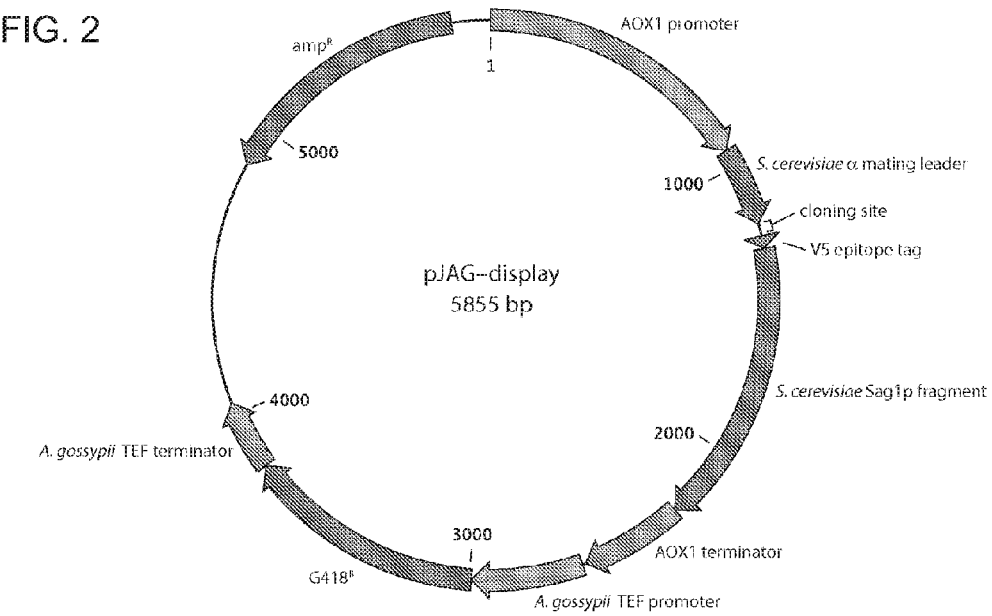

| Location | Feature | Origin |
|---|---|---|
| 1..939 | Eukaryotic Promoter | *Pichia pastoris* AOX1 promoter |
| 940..1206 | Open Reading Frame | *S. cerevisiae* α mating factor leader |
| 1207..1248 | Cloning Site | Bsu I – Xho I – Not I – Bsu I |
| 1249..1290 | Open Reading Frame | V5 epitope tag |
| 1291..2253 | Open Reading Frame | *S. cerevisiae* SAG1 gene fragment |
| 2254..2603 | Eukaryotic Terminator | *Pichia pastoris* AOX1 terminator |
| 2615..2993 | Eukaryotic Promoter | *Ashbya gossypii* TEF promoter |
| 2994..3803 | Open Reading Frame | G418 resistance protein |
| 3804..4040 | Eukaryotic Terminator | *Ashbya gossypii* TEF terminator |
| complement 4863..5723 | Open Reading Frame | Ampicillin resistance protein |

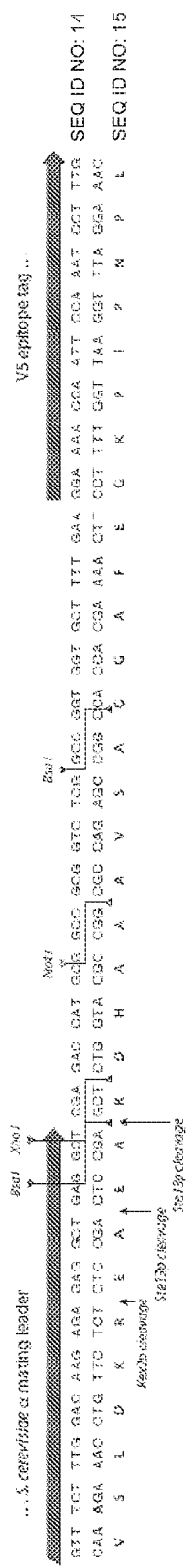
FIG. 3A
FIG. 3B

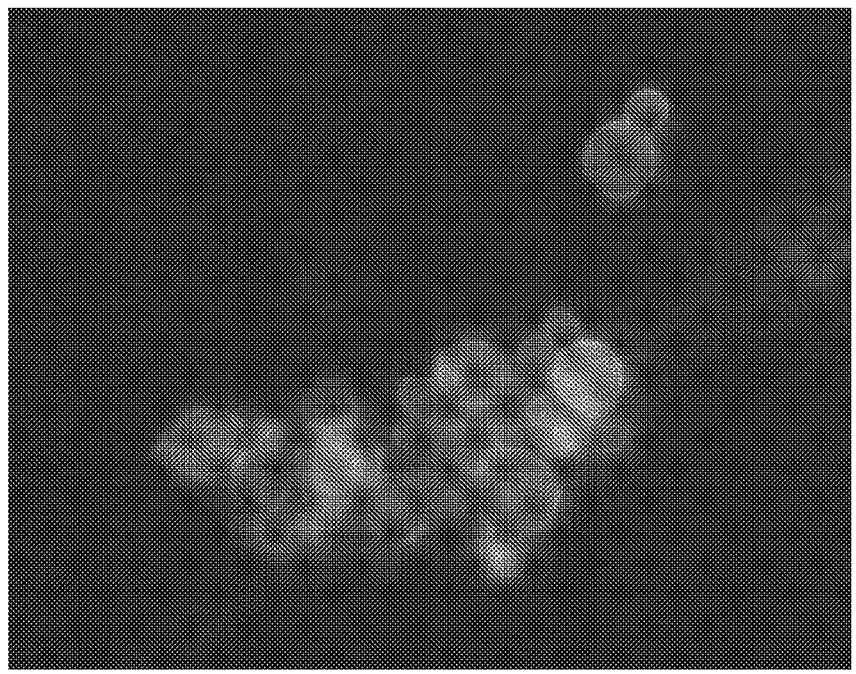
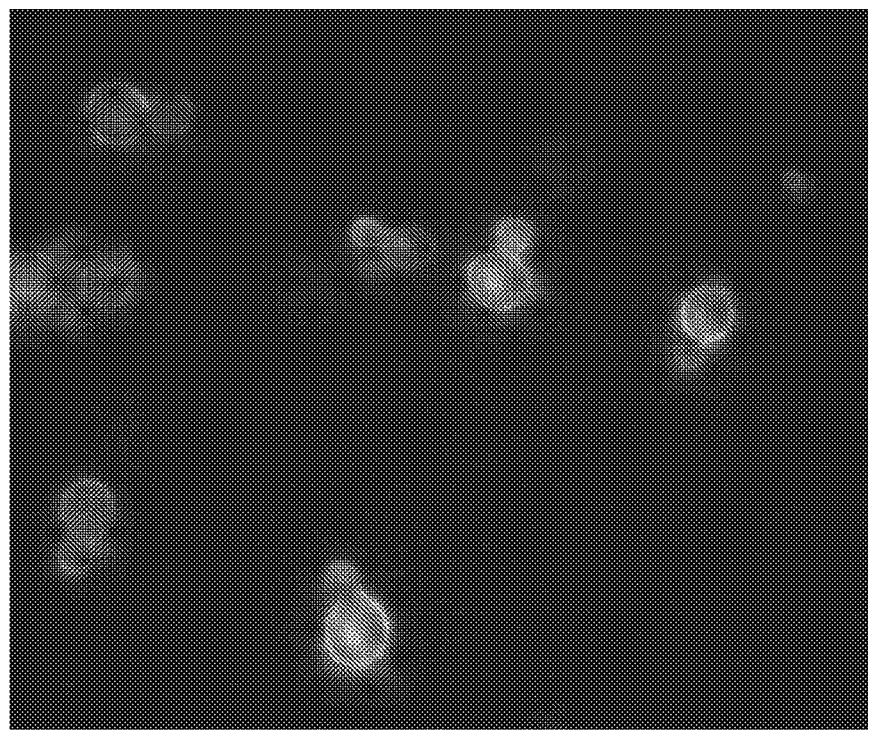
FIG. 7

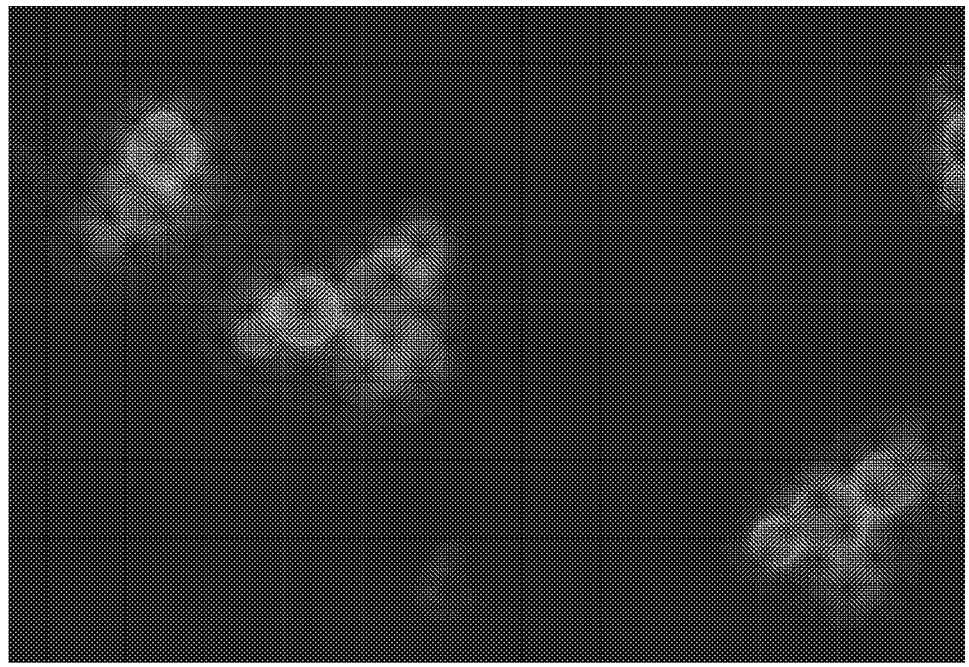
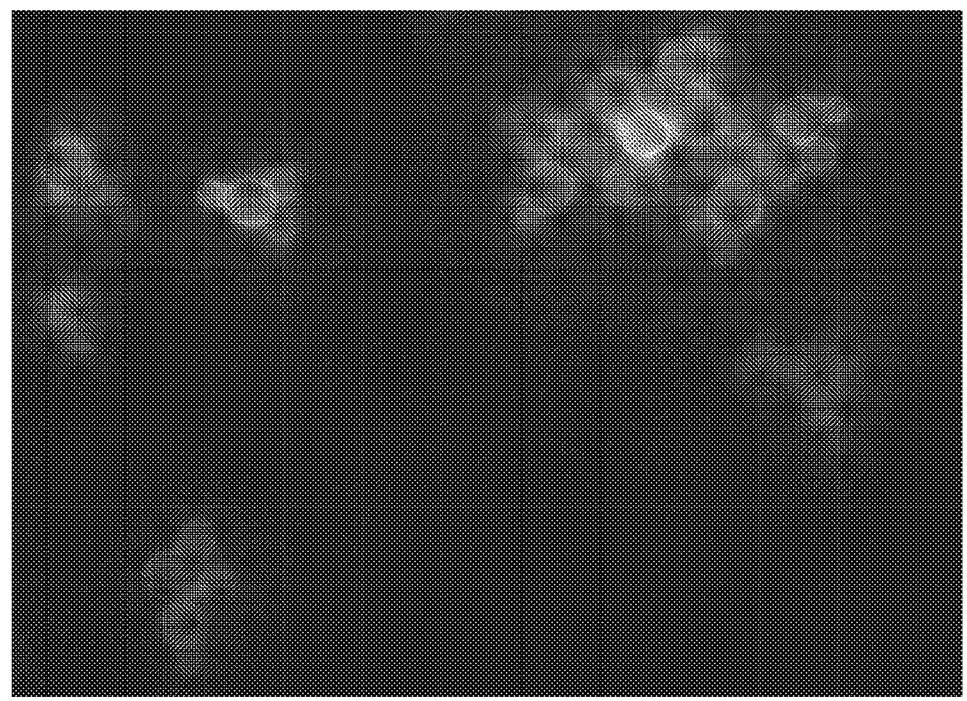
FIG. 8

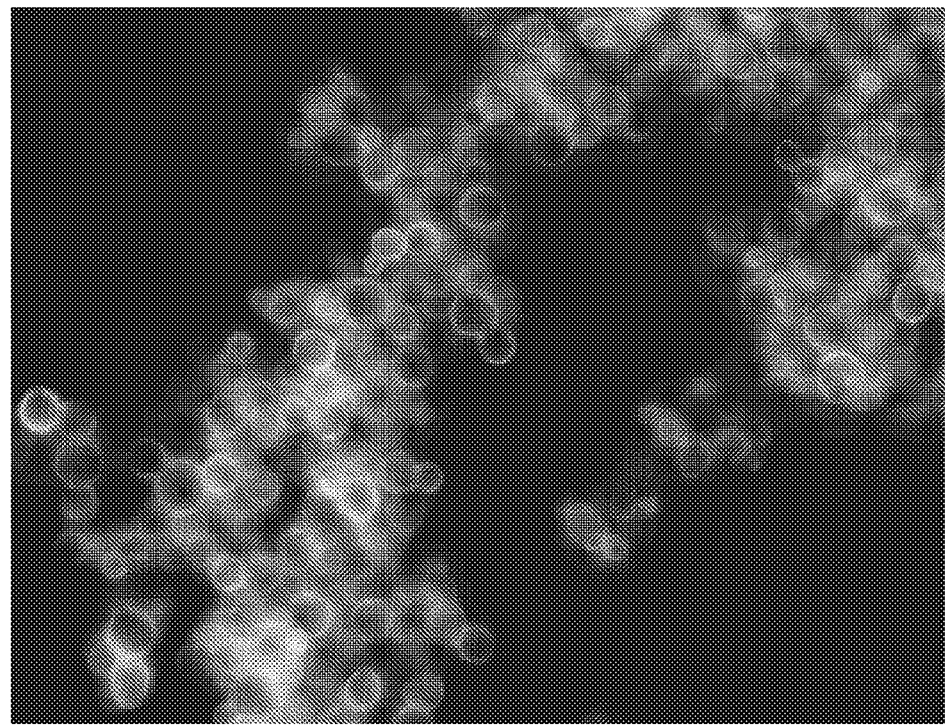
FIG. 9

SEQUENCE LISTING

<160> NUMBER OF SEQ ID NOS: 27

<210> SEQ ID NO 1
<211> LENGTH: 9865
<212> TYPE: DNA
<213> ORGANISM: Pichia pastoris

<400> SEQUENCE: 1

```
aacgtcaaag acagcaatgg agtcaatatt gataacacca ctggcagagc ggttcgtacg      60
tcgttttgga gccgatatga ggctcagcgt gctaacagca cgattgacaa gaagactctc     120
gagtgacagt aggttgagta agtattcgc ttagattccc aaccttcgtt ttattctttc      180
gtagacaaag aagctgcatg cgaacatagg gacaactttt ataaatccaa ttgtcaaacc     240
aacgtaaaac cctctggcac cattttcaac atatatttgt gaagcagtac gcaatatcga     300
taaatactca ccgttgtttg taacagcccc aacttgcata cgccttctaa tgacctcaaa     360
tggataagcc gcagcttgtg ctaacatacc agcagcaccg cccgcggtca gctgcgccca     420
cacatataaa ggcaatctac gatcatggga ggaattagtt ttgaccgtca ggtcttcaag     480
agttttgaac tcttcttctt gaactgtgta acctttttaaa tgacgggatc taaatacgtc    540
atggatgaga tcatgtgtgt aaaaactgac tccagcatat ggaatcattc caaagattgt    600
aggagcgaac ccacgataaa agtttcccaa ccttgccaaa gtgtctaatg ctgtgacttg    660
aaatctgggt tcctcgttga agaccctgcg tactatgccc aaaaactttc ctccacgagc    720
cctattaact tctctatgag tttcaaatgc caaacggaca cggattaggt ccaatgggta    780
agtgaaaaac acagagcaaa ccccagctaa tgagccggcc agtaaccgtc ttggagctgt    840
ttcataagag tcattaggga tcaataacgt tctaatctgt tcataacata caaattttat    900
ggctgcatag ggaaaaattc tcaacagggt agccgaatga ccctgatata gacctgcgac    960
accatcatac ccatagatct gcctgacagc cttaaagagc ccgctaaaag acccggaaaa   1020
ccgagagaac tctggattag cagtctgaaa aagaatcttc actctgtcta gtggagcaat   1080
taatgtctta gcggcacttc ctgctactcc gccagctact cctgaataga tcacatactg   1140
caaagactgc ttgtcgatga ccttggggtt atttagcttc aagggcaatt tttgggacat   1200
tttggacaca ggagactcag aaacagacac agagcgttct gagtcctggt gctcctgacg   1260
taggcctaga acaggaatta ttggctttat ttgtttgtcc atttcatagg cttggggtaa   1320
tagatagatg acagagaaat agagaagacc taatatttt tgttcatggc aaatcgcggg    1380
ttcgcggtcg ggtcacacac ggagaagtaa tgagaagagc tggtaatctg gggtaaaagg   1440
gttcaaaaga aggtcgcctg gtagggatgc aatacaaggt tgtcttggag tttacattga   1500
ccagatgatt tggctttttc tctgttcaat tcacattttt cagcgagaat cggattgacg    1560
gagaaatggc ggggtgtggg gtggatagat ggcagaaatg ctcgcaatca ccgcgaaaga   1620
aagactttat ggaatagaac tactgggtgg tgtaaggatt acatagctag tccaatggag   1680
tccgttggaa aggtaagaag aagctaaaac cggctaagta actagggaag aatgatcaga   1740
cttttgatttg atgaggtctg aaaatactct gctgctttt cagttgcttt ttccctgcaa    1800
cctatcattt tccttttcat aagcctgcct tttctgtttt cacttatatg agttccgccg   1860
agacttcccc aaattctctc ctggaacatt ctctatcgct ctccttccaa gttgcgcccc   1920
ctggcactgc ctagtaatat taccacgcga cttatattca gttccacaat ttccagtgtt   1980
cgtagcaaat atcatcagcc taccgttcgt atagcataca ttatacgaac ggtacttttt   2040
tgtagaaatg tcttggtgtc ctcgtccaat caggtagcca tctctgaaat atctggctcc   2100
```

```
gttgcaactc cgaacgacct gctggcaacg taaaattctc cggggtaaaa cttaaatgtg    2160
gagtaatgga accagaaacg tctcttccct tctctctcct tccaccgccc gttaccgtcc    2220
ctaggaaatt ttactctgct ggagagcttc ttctacggcc cccttgcagc aatgctcttc    2280
ccagcattac gttgcgggta aaacggaggt cgtgtacccg acctagcagc ccagggatgg    2340
aaaagtcccg gccgtcgctg gcaataatag cgggcggacg catgtcatga gattattgga    2400
aaccaccaga atcgaatata aaaggcgaac acctttccca attttggttt ctcctgaccc    2460
aaagacttta aatttaattt atttgtccct atttcaatca attgaacaac tatttcgcga    2520
aacgatgaga tttccttcaa tttttactgc tgttttattc gcagcatcct ccgcattagc    2580
tgctccagtc aacactacaa cagaagatga aacggcacaa attccggctg aagctgtcat    2640
cggttactca gatttagaag gggatttcga tgttgctgtt ttgccatttt ccaacagcac    2700
aaataacggg ttattgttta taaatactac tattgccagc attgctgcta agaagaagg     2760 ggtatctctc gagaaaagag aggctgaagc tgaattcgcc acaaaacgtg gatctcccaa    2820
ccctacgagg gcggcagcag tcaaggccgc attccagacg tcgtggaacg cttaccacca    2880
ttttgccttt ccccatgacg acctccaccc ggtcagcaac agctttgatg atgagagaaa    2940
cggctggggc tcgtcggcaa tcgatggctt ggacacggct atcctcatgg gggatgccga    3000
cattgtgaac acgatccttc agtatgtacc gcagatcaac ttcaccacga ctgcggttgc    3060
caaccaaggc atctccgtgt cgagaccaa cattcggtac ctcggtggcc tgctttctgc     3120
ctatgacctg ttgcgaggtc ctttcagctc cttggcgaca aaccagaccc tggtaaacag    3180
ccttctgagg caggctcaaa cactggccaa cggcctcaag gttgcgttca ccactcccag    3240
cggtgtcccg gaccctaccg tcttcttcaa ccctactgtc cggagaagtg gtgcatctag    3300
caacaacgtc gctgaaattg gaagcctggt gctcgagtgg acacggttga gcgacctgac    3360
gggaaacccg cagtatgccc agcttgcgca gaagggcgag tcgtatctcc tgaatccaaa    3420
gggaagcccg gaggcatggc ctggcctgat tggaacgttt gtcagcacga gcaacggtac    3480 cttcaggat agcagcggca gctggtccgg cctcatggac agcttctacg agtacctgat       3540
caagatgtac ctgtacgacc cggttgcgtt tgcacactac aaggatcgct gggtccttgc     3600
tgccgactcg accattgcgc atctccgcctc tcacccgtcg acgcgcaagg acttgacctt    3660
tttgtcttcg tacaacggac agtctacgtc gccaaactca ggacatttgg ccagttttgc    3720
cggtggcaac ttcatcttgg gaggcattct cctgaacgag caaaagtaca ttgactttgg    3780
aatcaagctt gccagctcgt actttgccac gtacaaccag acggcttctg gaatcggccc    3840
cgaaggcttc gcgtgggtgg acagcgtgac gggcgccggc ggctcgccgc cctcgtccca    3900
gtccgggttc tactcgtcgg caggattctg ggtgacggca ccgtattaca tcctgcggcc    3960
ggagacgctg gagagcttgt actacgcata ccgcgtcacg ggcgactcca gtggcagga    4020 cctggcgtgg gaagcgttca gtgccattga ggacgcatgc cgcgccggca gcgcgtactc    4080
gtccatcaac gacgtgacgc aggccaacgg cggggggtgcc tctgacgata tggagagctt    4140
ctggtttgcc gaggcgctca gtatgcgta cctgatcttt gcggaggagt cggatgtgca    4200
ggtgcaggcc aacggcggga acaaatttgt ctttaacacg gaggcgcacc cctttagcat    4260
ccgttcatca tcacgacggg gcggccacct tgctcacgac gagttgtaat ctagggcggc    4320
cgccagcttg ggcccgaaca aaactcatc tcagaagagg atctgaatag cgccgtcgac    4380
catcatcatc atcatcattg agttttagcc ttagacatga ctgttcctca gttcaagttg    4440
```

```
ggcacttacg agaagaccgg tcttgctaga ttctaatcaa gaggatgtca gaatgccatt    4500
tgcctgagag atgcaggctt cattttttgat acttttttat ttgtaaccta tatagtatag    4560 gattttttt gtcattttgt ttcttctcgt acgagcttgc tcctgatcag cctatctcgc    4620
agctgatgaa tatcttgtgg taggggtttg ggaaaatcat tcgagtttga tgttttttctt   4680 ggtatttccc actcctcttc agagtacaga agattaagtg agaccttcgt ttgtgcggat    4740
cccccacaca ccatagcttc aaaatgtttc tactcctttt ttactcttcc agattttctc    4800
ggactccgcg catcgccgta ccacttcaaa acacccaagc acagcatact aaatttcccc    4860
tctttcttcc tctagggtgt cgttaattac ccgtactaaa ggtttggaaa agaaaaaaga    4920
gaccgcctcg tttcttttc ttcgtcgaaa aaggcaataa aaattttat cacgtttctt     4980 tttcttgaaa attttttttt ttgattttt tctctttcga tgacctccca ttgatattta    5040
agttaataaa cggtcttcaa tttctcaagt ttcagtttca ttttttcttgt tctattacaa   5100 cttttttac ttcttgctca ttagaaagaa agcatagcaa tctaatctaa gggcggtgtt    5160
gacaattaat catcggcata gtatatcggc atagtataat acgacaaggt gaggaactaa    5220
accatggcca agcctttgtc tcaagaagaa tccaccctca ttgaaagagc aacggctaca    5280
atcaacagca tccccatctc tgaagactac agcgtcgcca cgcagctct ctctagcgac     5340 ggccgcatct tcactggtgt caatgtatat cattttactg ggggaccttg tgcagaactc    5400
gtggtgctgg gcactgctgc tgctgcggca gctggcaacc tgacttgtat cgtcgcgatc    5460
ggaaatgaga acaggggcat cttgagcccc tgcggacggt gccgacaggt gcttctcgat    5520
ctgcatcctg ggatcaaagc catagtgaag gacagtgatg gacagccgac ggcagttggg    5580
attcgtgaat tgctgccctc tggttatgtg tgggagggct aagcacttcg tggccgagga    5640
gcaggactga cacgtccgac gcggcccgac gggtccgagg cctcggagat ccgtcccct    5700 tttcctttgt cgatatcatg taattagtta tgtcacgctt acattcacgc cctccccca    5760 catccgctct aaccgaaaag gaaggagtta gacaacctga agtctaggtc cctatttatt    5820
tttttatagt tatgttagta ttaagaacgt tatttatatt tcaaattttt ctttttttc    5880 tgtacagacg cgtgtacgca tgtaacatta tactgaaaac cttgcttgag aaggttttgg    5940
gacgctcgaa ggctttaatt tgcaagctgg agaccaacat gtgagcaaaa ggccagcaaa    6000
aggccaggaa ccgtaaaaag gccgcgttgc tggcgttttt ccataggctc cgccccctg    6060 acgagcatca caaaaatcga cgctcaagtc agaggtggcg aaacccgaca ggactataaa    6120
gataccaggc gtttccccct ggaagctccc tcgtgcgctc tcctgttccg accctgccgc    6180
ttaccggata cctgtccgcc tttctccctt cgggaagcgt ggcgctttct catagctcac    6240
gctgtaggta tctcagttcg gtgtaggtcg ttcgctccaa gctgggctgt gtgcacgaac    6300 ccccgttca gcccgaccgc tgcgccttat ccggtaacta tcgtcttgag tccaacccgg    6360
taagacacga cttatcgcca ctggcagcag ccactggtaa caggattagc agagcgaggt    6420
atgtaggcgg tgctacagag ttcttgaagt ggtggcctaa ctacggctac actagaagaa    6480
cagtatttgg tatctgcgct ctgctgaagc cagttacctt cggaaaaaga gttggtagct    6540
cttgatccgg caaacaaacc accgctggta gcggtggttt ttttgtttgc aagcagcaga    6600
ttacgcgcag aaaaaaagga tctcaagaag atcctttgat cttttctacg ggtctgacg    6660 ctcagtggaa cgaaaactca cgttaaggga ttttggtcat gagatcagat ctaacatcca    6720
taatcgtatt cgccgtttct gtcatttgcg ttttgtacgg accctcacaa caattatcat    6780
ctccaaaaat agactatgat ccattgacgc tccgatcact tgatttgaag actttggaag    6840
```

```
ctccttcaca gttgagtcca ggcaccgtag aagataatct tcgaagacaa ttggagtttc    6900
attttcctta ccgcagttac gaaccttttc cccaacatat ttggcaaacg tggaaagttt    6960
ctccctctga tagttccttt ccgaaaaact tcaaagactt aggtgaaagt tggctgcaaa    7020
ggtccccaaa ttatgatcat tttgtgatac ccgatgatgc agcatgggaa cttattcacc    7080
atgaatacga acgtgtacca gaagtcttgg aagctttcca cctgctacca gagcccattc    7140
taaaggccga tttttcagg tatttgattc tttttgcccg tggaggactg tatgctgaca    7200
tggacactat gttattaaaa ccaatagaat cgtggctgac tttcaatgaa actattggtg    7260
gagtaaaaaa caatgctggg ttggtcattg gtattgaggc tgatcctgat agacctgatt    7320
ggcacgactg gtatgctaga aggatacaat tttgccaatg ggcaattcag tccaaacgag    7380
gacacccagc actgcgtgaa ctgattgtaa gagttgtcag cacgacttta cggaaagaga    7440
aaagcggtta cttgaacatg gtggaaggaa aggatcgtgg aagtgatgtg atggactgga    7500
cgggtccagg aatatttaca gacactctat ttgattatat gactaatgtc aatacaacag    7560
gccactcagg ccaaggaatt ggagctggct cagcgtatta caatgcctta tcgttggaag    7620
aacgtgatgc cctctctgcc cgcccgaacg gagagatgtt aaaagagaaa gtcccaggta    7680
aatatgcaca gcaggttgtt ttatgggaac aatttaccaa cctgcgctcc cccaaattaa    7740
tcgacgatat tcttattctt ccgatcacca gcttcagtcc agggattggc acagtggag    7800 ctggagattt gaaccatcac cttgcatata ttaggcatac atttgaagga agttggaagg    7860
actaaagaaa gctagagtaa aatagatata gcgagattag agaatgaata ccttcttcta    7920
agcgatcgtc cgtcatcata gaatatcatg gactgtatag tttttttttt gtacatataa    7980
tgattaaacg gtcatccaac atctcgttga cagatctctc agtacgcgaa atccctgact    8040
atcaaagcaa gaaccgatga agaaaaaaac aacagtaacc caaacaccac aacaaacact    8100
ttatcttctc ccccccaaca ccaatcatca aagagatgtc ggaaccaaac accaagaagc    8160
aaaaactaac cccatataaa aacatcctgg tagataatgc tggtaacccg ctctccttcc    8220
atattctggg ctacttcacg aagtctgacc ggtctcagtt gatcaacatg atcctcgaaa    8280
tgggtggcaa gatcgttcca gacctgcctc ctctggtaga tggagtgttg tttttgacag    8340
gggattacaa gtctattgat gaagataccc taaagcaact gggggacgtt ccaatataca    8400
gagactcctt catctaccag tgttttgtgc acaagacatc tcttcccatt gacactttcc    8460
gaattgacaa gaacgtcgac ttggctcaag atttgatcaa tagggcccct caagagtctg    8520
tggatcatgt cacttctgcc agcacagctg cagctgctgc tgttgttgtc gctaccaacg    8580
gcctgtcttc taaaccagac gctcgtacta gcaaaataca gttcactccc gaagaagatc    8640
gttttattct tgactttgtt aggagaaatc ctaaacgaag aaacacacat caactgtaca    8700
ctgagctcgc tcagcacatg aaaaaccata cgaatcattc tatccgccac agatttcgtc    8760
gtaatctttc cgctcaactt gattgggttt atgatatcga tccattgacc aaccaacctc    8820
gaaaagatga aaacgggaac tacatcaagg tacaagatct tccacaagga attcgtggtc    8880
attattctgc ccaagatgat tacaatttgt gtttatcggt tcaaccttc attgaatctg    8940 tagatgagac aacaggccaa gaattttca aacctctgaa aggtgtattt gatgacttgg    9000
aatctcgctt tcctcaccat acaaagactt cctggagaga cagattcaga aagtttgcct    9060
ctaaatacgg tgttcgtcag tacatcgcgt attatgaaaa gactgttgaa ctcaatggtg    9120
ttcctaatcc gatgacgaac tttacctcaa aggcttccat tgaaaaattt agagaaagac    9180
```

-continued

```
gcgggacttc acgtaacagt ggccttccag gcccggttgg tgtagaagct gtaagctctt    9240
tggaccacat atccccattg gtcacatcta attccaattc tgcagctgct gcagctgctg    9300
ccgcagcagt tgcagcctct gcctctgctt cttcagctcc taatacttca actaccaatt    9360
tctttgaaca ggagaatatt gcccaagttc tctctgcaca taacaacgag cagtctattg    9420
cagaagttat tgagtccgca cagaatgtca acacccatga aagtgaacct atagctgatc    9480
atgttcgaaa aaatcttaca gacgatgaat tgcttgacaa aatggatgat attttaagct    9540
ccagaagtct aggcggacta gatgacttga taaagatcct ctacactgag ctgggatttg    9600
ctcatcgtta taccgaattt cttttacct catgttctgg tgatgtgatt ttcttccgac     9660
cattagtgga acatttcctt cttactggtg agtgggagct ggagaatact cgtggcatct    9720
ggaccggtcg tcaagacgaa atgctacgtc tagcaatct agatgacctg cacaagttaa    9780
ttgacctgca tgggaaagaa cgtgttgaga ccagaagaaa agccatcaag ggagaatgat    9840
cataagaaat gaaaaacgta taagt                                          9865
```

<210> SEQ ID NO 2
<211> LENGTH: 404
<212> TYPE: PRT
<213> ORGANISM: Pichia pastoris

<400> SEQUENCE: 2

```
Met Ala Lys Ala Asp Gly Ser Leu Leu Tyr Tyr Asn Pro His Asn Pro
1               5                   10                  15

Pro Arg Arg Tyr Tyr Phe Tyr Met Ala Ile Phe Ala Val Ser Val Ile
            20                  25                  30

Cys Val Leu Tyr Gly Pro Ser Gln Gln Leu Ser Ser Pro Lys Ile Asp
        35                  40                  45

Tyr Asp Pro Leu Thr Leu Arg Ser Leu Asp Leu Lys Thr Leu Glu Ala
    50                  55                  60

Pro Ser Gln Leu Ser Pro Gly Thr Val Glu Asp Asn Leu Arg Arg Gln
65                  70                  75                  80

Leu Glu Phe His Phe Pro Tyr Arg Ser Tyr Glu Pro Phe Pro Gln His
                85                  90                  95

Ile Trp Gln Thr Trp Lys Val Ser Pro Ser Asp Ser Ser Phe Pro Lys
            100                 105                 110

Asn Phe Lys Asp Leu Gly Glu Ser Trp Leu Gln Arg Ser Pro Asn Tyr
        115                 120                 125

Asp His Phe Val Ile Pro Asp Asp Ala Ala Trp Glu Leu Ile His His
    130                 135                 140

Glu Tyr Glu Arg Val Pro Glu Val Leu Glu Ala Phe His Leu Leu Pro
145                 150                 155                 160

Glu Pro Ile Leu Lys Ala Asp Phe Phe Arg Tyr Leu Ile Leu Phe Ala
                165                 170                 175

Arg Gly Gly Leu Tyr Ala Asp Met Asp Thr Met Leu Leu Lys Pro Ile
            180                 185                 190

Glu Ser Trp Leu Thr Phe Asn Glu Thr Ile Gly Gly Val Lys Asn Asn
        195                 200                 205

Ala Gly Leu Val Ile Gly Ile Glu Ala Asp Pro Asp Arg Pro Asp Trp
    210                 215                 220

His Asp Trp Tyr Ala Arg Arg Ile Gln Phe Cys Gln Trp Ala Ile Gln
225                 230                 235                 240

Ser Lys Arg Gly His Pro Ala Leu Arg Glu Leu Ile Val Arg Val Val
                245                 250                 255
```

```
Ser Thr Thr Leu Arg Lys Glu Lys Ser Gly Tyr Leu Asn Met Val Glu
                260                 265                 270

Gly Lys Asp Arg Gly Ser Asp Val Met Asp Trp Thr Gly Pro Gly Ile
            275                 280                 285

Phe Thr Asp Thr Leu Phe Asp Tyr Met Thr Asn Val Asn Thr Thr Gly
        290                 295                 300

His Ser Gly Gln Gly Ile Gly Ala Gly Ser Ala Tyr Tyr Asn Ala Leu
305                 310                 315                 320

Ser Leu Glu Glu Arg Asp Ala Leu Ser Ala Arg Pro Asn Gly Glu Met
                325                 330                 335

Leu Lys Glu Lys Val Pro Gly Lys Tyr Ala Gln Gln Val Val Leu Trp
            340                 345                 350

Glu Gln Phe Thr Asn Leu Arg Ser Pro Lys Leu Ile Asp Asp Ile Leu
        355                 360                 365

Ile Leu Pro Ile Thr Ser Phe Ser Pro Gly Ile Gly His Ser Gly Ala
370                 375                 380

Gly Asp Leu Asn His His Leu Ala Tyr Ile Arg His Thr Phe Glu Gly
385                 390                 395                 400

Ser Trp Lys Asp

<210> SEQ ID NO 3
<211> LENGTH: 5475
<212> TYPE: DNA
<213> ORGANISM: Artificial Sequence
<220> FEATURE:
<223> OTHER INFORMATION: Synthetic Oligonucleotide

<400> SEQUENCE: 3
cgactattat cgatcaatga aatccatcaa gattgaaatc ttaaaattgc ccctttcact      60
tgacaggatc cttttttgta gaaatgtctt ggtgtcctcg tccaatcagg tagccatctc    120
tgaaatatct ggctccgttg caactccgaa cgacctgctg caacgtaaaa attccccggg    180
gtaaaactta aatgtggagt aatggaacca gaaacgtctc ttcccttctc tctccttcca    240
ccgcccgtta ccgtccctag gaaattttac tctgctggag agcttcttct acggccccct    300
tgcagcaatg ctcttcccag cattacgttg cgggtaaaac ggaggtcgtg tacccgacct    360
agcagcccag ggatgaaaaa gtcccggccg tcgctggcaa taatagcggg cggacgcatg    420
tcatgagatt attggaaacc accagaatcg aatataaaag gcgaacacct ttcccaattt    480
tggtttctcc tgacccaaag actttaaatt taatttattt gtccctattt caatcaattg    540
aacaactatc aaaacacgat gagattccca tctatttttca ctgctgtttt gttcgctgct    600
tcttctgctt tggctgctcc agttaacact actactgagg acgagactgc tcaaattcca    660
gctgaggctg ttattggtta cttggacttg gagggtgact tcgacgttgc tgttttgcca    720
ttctctaact ctactaacaa cggtttgttg ttcattaaca ctactattgc ttctattgct    780
gctaaggagg agggtgtttc tttggacaag agagaggctg aggctcgaga ccatgcggcc    840
gcggtctcgg ccggtggtgc ttttgaagga aaaccaattc caaatccttt gttgggattg    900
gattctactt ctgccaaatc atctttcatt tcaaccacca ccactgattt gacttcaatc    960
aacacttctg cttactctac tggatctatt tcaactgttg aaactggaaa cagaaccact   1020
tctgaagtta tttctcatgt tgttaccact tccaccaaac tttctccaac tgctactact   1080
tctttgacca ttgctcaaac ttcaatttac tctactgatt ccaatatcac tgttggaact   1140
gatattcaca ccacttctga agttatttct gatgttgaaa ctatttcaag agaaactgct   1200
```

```
tctactgttg ttgctgctcc aacttccacc actggatgga ctggtgccat gaacacttat    1260
atttctcagt tcacttcttc ttcttttgcc actatcaact ctactccaat catttcttct    1320
tctgctgttt ttgaaacttc tgatgcttcc attgtcaatg ttcacactga aaatatcacc    1380
aacactgctg ctgttccatc tgaagagcca acttttgtca atgctactag aaactctttg    1440
aactcttttt gttcttccaa acaaccttct tctccttctt cttacacttc ttctcctttg    1500
gtttcttctt tgtctgtttc caaaactctt ttgtcaactt ctttcactcc ttctgttcca    1560
acttccaaca cttatatcaa aaccaagaac actggttatt tgaacacac tgctttgacc     1620 acttcttctg ttggtttgaa ctcttttagt gaaactgctg tttcttctca aggaaccaag    1680
attgatactt ttttggtttc ttctttgatt gcttatccat cttctgcttc tggatctcaa    1740
ttgtctggta ttcaacaaaa tttcacttcc acttctttga tgatttcaac ttatgaagga    1800
aaagcttcca ttttcttctc tgctgaactt ggatctatca ttttttttgtt gttgagttat    1860 cttttgtttt aatcaagagg atgtcagaat gccatttgcc tgagagatgc aggcttcatt    1920
tttgatactt ttttatttgt aacctatata gtataggatt ttttttgtca ttttgtttct    1980
tctcgtacga gcttgctcct gatcagccta tctcgcagct gatgaatatc ttgtggtagg    2040
ggtttgggaa atcattcga gtttgatgtt tttcttggta tttcccactc ctcttcagag     2100
tacagaagat taagtgacac gttcgtttgt gcaagcttca acgatgccaa aagggtataa    2160
taagcgtcat ttgcagcatt gtgaagaaaa ctatgtggca agccaagcct gcgaagaatg    2220
tagtcgagaa ttgagcttgc ctcgtccccg ccgggtcacc cggccagcga catggaggcc    2280 cagaatacc tccttgacag tcttgacgtg cgcagctcag gggcatgatg tgactgtcgc      2340
ccgtacattt agcccataca tccccatgta taatcatttg catccataca ttttgatggc    2400
cgcacggcgc gaagcaaaaa ttacggctcc tcgctgcaga cctgcgagca gggaaacgct    2460
cccctcacag acgcgttgaa ttgtccccac gccgcgcccc tgtagagaaa tataaaaggt    2520
taggatttgc cactgaggtt cttctttcat atacttcctt ttaaaatctt gctaggatac    2580
agttctcaca tcacatccga acataaacaa aaatgggtaa ggaaaagact cacgtttcca    2640
gaccaagatt gaactctaac atggacgctg acttgtacgg ttacaagtgg gctagagaca    2700
acgttggtca atctggtgct actatttaca gattgtacgg taagccagac gctccagagt    2760
tgttcttgaa gcacggtaag ggttctgttg ctaacgacgt tactgacgag atggttagat    2820
tgaactggtt gactgagttc atgccattgc caactattaa gcacttcatt agaactccag    2880
acgacgcttg gttgttgact actgctattc caggtaagac tgctttccaa gttttggagg    2940
agtacccaga ctctggtgag aacattgttg acgctttggc tgttttcttg agaagattgc    3000
actctattcc agtttgtaac tgtccattca actctgacag agttttcaga ttggctcaag    3060
ctcaatccag aatgaacaac ggtttggttg acgcttctga cttcgacgac gagagaaacg    3120
gttggccagt tgagcaagtt tggaaggaga tgcacaagtt gttgccattc tctccagact    3180
ctgttgttac tcacggtgac ttctcttttgg acaacttgat tttcgacgag ggtaagttga    3240
ttggttgtat tgacgttggt agagttggta ttgctgacag ataccaagac ttggctatt t   3300 tgtggaactg tttgggtgag ttctctccat cttttgcaaaa gagattgttc caaaagtacg    3360
gtattgacaa cccagacatg aacaagttgc aattccactt gatgttggac gagttcttct    3420
aaagtaactg acaataaaaa gattcttgtt ttcaagaact tgtcatttgt atagttttt     3480 tatattgtag ttgttctatt ttaatcaaat gttagcgtga tttatatttt ttttcgcctc    3540
```

| | |
|---|---|
| gacatcatct gcccagatgc gaagttaagt gcgcagaaag taatatcatg cgtcaatcgt | 3600 |
| atgtgaatgc tggtcgctat actgctgtcg attcgatact aacgccgcca tccagtgtcg | 3660 |
| gatctgtgag caaaaggcca gcaaaaggcc aggaaccgta aaaaggccgc gttgctggcg | 3720 |
| ttttccata ggctccgccc ccctgacgag catcacaaaa atcgacgctc aagtcagagg | 3780 |
| tgacgaaacc cgacaggact ataaagatac caggcgtttc ccctggaag ctccctcgtg | 3840 |
| cgctctcctg ttccgaccct gccgcttacc ggatacctgt ccgcctttct cccttcggga | 3900 |
| agcgtggcgc tttctcatag ctcacgctgt aggtatctca gttcggtgta ggtcgttcgc | 3960 |
| tccaagctgg gctgtgtgca cgaaccccc gttcagcccg accgctgcgc cttatccggt | 4020 |
| aactatcgtc ttgagtccaa cccggtaaga cacgacttat cgccactggc agcagccact | 4080 |
| ggtaacagga ttagcagagc gaggtatgta ggcggtgcta cagagttctt gaagtggtgg | 4140 |
| cctaactacg gctacactag aagaacagta tttggtatct gcgctctgct gaagccagtt | 4200 |
| accttcggaa aaagagttgg tagctcttga tccggcaaac aaaccaccgc tggtagcggt | 4260 |
| ggtttttttg tttgcaagca gcagattacg cgcagaaaaa aaggatctca agaagatcct | 4320 |
| ttgatctttt ctacggggtc tgacgctcag tggaacgaaa actcacgtta agggattttg | 4380 |
| gtcatgagat tatcaaaaag gatcttcacc tagatccttt ttaattaaaa atgaagattt | 4440 |
| aaatcaatct aaagtatata tgagtaaact tggtctgaca gttaccaatg cttaatcagt | 4500 |
| gaggcaccta tctcagcgat ctgtctattt cgttcatcca tagttgcctg actcccgtc | 4560 |
| gtgtagataa ctacgatacg ggagggctta ccatctggcc ccagtgctgc aatgataccg | 4620 |
| cgagatccac gctcaccggc tccagattta tcagcaataa accagccggc cggaagggcc | 4680 |
| gagcgcagaa gtgggccggc cactttatcc gcctccatcc agtctattaa ttgttgccgg | 4740 |
| gaagctagag taagtagttc gccagttaat agtttgcgca acgttgttgc cattgctaca | 4800 |
| ggcatcgtgg tgtcacgctc gtcgtttggt atggcttcat tcagctccgg ttcccaacga | 4860 |
| tcaaggcgag ttacatgatc ccccatgttg tgcaaaaaag cggttagctc cttcggtcct | 4920 |
| ccgatcgttg tcagaagtaa gttggccgca gtgttatcac tcatggttat ggcagcactg | 4980 |
| cataattctc ttactgtcat gccatccgta agatgctttt ctgtgactgg tgagtactca | 5040 |
| accaagtcat tctgagaata gtgtatgcgg cgaccgagtt gctcttgccc ggcgtcaata | 5100 |
| cgggataata ccgcgccaca tagcagaact ttaaaagtgc tcatcattgg aaaacgttct | 5160 |
| tcggggcgaa aactctcaag gatcttaccg ctgttgagat ccagttcgat gtaacccact | 5220 |
| cgtgcaccca actgatcttc agcatctttt actttcacca gcgtttctgg gtgagcaaaa | 5280 |
| acaggaaggc aaaatgccgc aaaaaaggga ataagggcga cacggaaatg ttgaatactc | 5340 |
| atactcttcc ttttcaata ttattgaagc atttatcagg gttattgtct catgagcgga | 5400 |
| tacatatttg aatgtattta gaaaaataaa caaatagggg ttccgcgcac atttccccga | 5460 |
| aaagtgccac ctggg | 5475 |

<210> SEQ ID NO 4
<211> LENGTH: 5855
<212> TYPE: DNA
<213> ORGANISM: Artificial Sequence
<220> FEATURE:
<223> OTHER INFORMATION: Synthetic Oligonucleotide

<400> SEQUENCE: 4

| | |
|---|---|
| gatctaacat ccaaagacga aaggttgaat gaaacctttt tgccatccga catccacagg | 60 |
| tccattctca cacataagtg ccaaacgcaa caggagggga tacactagca gcagaccgtt | 120 |

```
gcaaacgcag gacctccact cctcttctcc tcaacaccca cttttgccat cgaaaaacca    180
gcccagttat tgggcttgat tggagctcgc tcattccaat tccttctatt aggctactaa    240
caccatgact ttattagcct gtctatcctg gccccctgg cgaggttcat gtttgtttat     300
ttccgaatgc aacaagctcc gcattacacc cgaacatcac tccagatgag ggctttctga    360
gtgtggggtc aaatagtttc atgttcccca aatggcccaa aactgacagt ttaaacgctg    420
tcttggaacc taatatgaca aaagcgtgat ctcatccaag atgaactaag tttggttcgt    480
tgaaatgcta acggccagtt ggtcaaaaag aaacttccaa aagtcggcat accgtttgtc    540
ttgtttggta ttgattgacg aatgctcaaa aataatctca ttaatgctta gcgcagtctc    600
tctatcgctt ctgaaccccg gtgcacctgt gccgaaacgc aaatggggaa cacccgctt    660 tttgatgat tatgcattgt ctccacattg tatgcttcca agattctggt gggaatactg    720
ctgatagcct aacgttcatg atcaaaattt aactgttcta cccctactt gacagcaata    780 tataaacaga aggaagctgc cctgtcttaa acctttttt ttatcatcat tattagctta     840 cttcataat tgcgactggt tccaattgac aagcttttga ttttaacgac ttttaacgac     900
aacttgagaa gatcaaaaaa caactaatta ttcgaaacga tgagattccc atctatttc    960 actgctgttt tgttcgctgc ttcttctgct ttggctgctc cagttaacac tactactgag    1020
gacgagactg ctcaaattcc agctgaggct gttattggtt acttggactt ggagggtgac    1080
ttcgacgttg ctgttttgcc attctctaac tctactaaca acggtttgtt gttcattaac    1140
actactattg cttctattgc tgctaaggag gagggtgttt cttttggacaa gagagaggct    1200 gaggctcgag accatgcggc cgcggtctcg gccggtggtg cttttgaagg aaaaccaatt    1260
ccaaatcctt tgttgggatt ggattctact tctgccaaat catctttcat ttcaaccacc    1320
accactgatt tgacttcaat caacacttct gcttactcta ctggatctat ttcaactgtt    1380
gaaactggaa acagaaccac ttctgaagtt atttctcatg ttgttaccac ttccaccaaa    1440 cttctccaa ctgctactac ttcttgacc attgctcaaa cttcaattta ctctactgat     1500
tccaatatca ctgttggaac tgatattcac accacttctg aagttatttc tgatgttgaa    1560
actatttcaa gagaaactgc ttctactgtt gttgctgctc caacttccac cactggatgg    1620
actggtgcca tgaacactta tatttctcag ttcacttctt cttctttgc cactatcaac     1680 tctactccaa tcatttcttc ttctgctgtt tttgaaactt ctgatgcttc cattgtcaat    1740
gttcacactg aaaatatcac caacactgct gctgttccat ctgaagagcc aacttttgtc    1800
aatgctacta gaaactcttt gaactctttt tgttcttcca acaaccttc ttctccttct     1860 tcttacactt cttctccttt ggtttcttct ttgtctgttt ccaaaactct tttgtcaact    1920
tctttcactc cttctgttcc aacttccaac acttatatca aaaccaagaa cactggttat    1980
tttgaacaca ctgctttgac cacttcttct gttggtttga actcttttag tgaaactgct    2040
gtttcttctc aaggaaccaa gattgatact ttttggttt cttctttgat tgcttatcca    2100
tcttctgctt ctggatctca attgtctggt attcaacaaa atttcacttc acttctttg    2160 atgatttcaa cttatgaagg aaaagcttcc attttcttct ctgctgaact tggatctatc    2220
atttttttgt tgttgagtta tcttttgttt taatcaagag gatgtcagaa tgccatttgc    2280
ctgagagatg caggcttcat ttttgatact ttttatttg taacctatat agtataggat    2340 ttttttttgtc atttttgttc ttctcgtacg agcttgctcc tgatcagcct atctcgcagc    2400
tgatgaatat cttgtggtag gggtttggga aaatcattcg agtttgatgt ttttcttggt    2460
```

```
atttcccact cctcttcaga gtacagaaga ttaagtgaca cgttcgtttg tgcaagcttc    2520
aacgatgcca aaagggtata ataagcgtca tttgcagcat tgtgaagaaa actatgtggc    2580
aagccaagcc tgcgaagaat gtagtcgaga attgagcttg cctcgtcccc gccgggtcac    2640
ccggccagcg acatggaggc ccagaatacc ctccttgaca gtcttgacgt gcgcagctca    2700
ggggcatgat gtgactgtcg cccgtacatt tagcccatac atccccatgt ataatcattt    2760
gcatccatac attttgatgg ccgcacggcg cgaagcaaaa attacggctc ctcgctgcag    2820
acctgcgagc agggaaacgc tcccctcaca gacgcgttga attgtcccca cgccgcgccc    2880
ctgtagagaa atataaaagg ttaggatttg ccactgaggt tcttcttttca tatacttcct    2940 tttaaaatct tgctaggata cagttctcac atcacatccg aacataaaca aaaatgggta    3000
aggaaaagac tcacgtttcc agaccaagat tgaactctaa catggacgct gacttgtacg    3060
gttacaagtg ggctagagac aacgttggtc aatctggtgc tactatttac agattgtacg    3120
gtaagccaga cgctccagag ttgttcttga agcacggtaa gggttctgtt gctaacgacg    3180
ttactgacga gatggttaga ttgaactggt tgactgagtt catgccattg ccaactatta    3240
agcacttcat tagaactcca gacgacgctt ggttgttgac tactgctatt ccaggtaaga    3300 ctgcttttcca agttttggag gagtacccag actctggtga gaacattgtt gacgctttgg    3360
ctgttttctt gagaagattg cactctattc cagtttgtaa ctgtccattc aactctgaca    3420
gagttttcag attggctcaa gctcaatcca gaatgaacaa cggtttggtt gacgcttctg    3480
acttcgacga cgagagaaac ggttggccag ttgagcaagt ttggaaggag atgcacaagt    3540
tgttgccatt ctctccagac tctgttgtta ctcacggtga cttctctttg gacaacttga    3600
ttttcgacga gggtaagttg attggttgta ttgacgttgg tagagttggt attgctgaca    3660
gataccaaga cttggctatt ttgtggaact gtttgggtga gttctctcca tctttgcaaa    3720
agagattgtt ccaaaagtac ggtattgaca acccagacat gaacaagttg caattccact    3780
tgatgttgga cgagttcttc taaagtaact gacaataaaa agattcttgt tttcaagaac    3840
ttgtcatttg tatagttttt ttatattgta gttgttctat tttaatcaaa tgttagcgtg    3900
atttatattt tttttcgcct cgacatcatc tgccccagatg cgaagttaag tgcgcagaaa    3960
gtaatatcat gcgtcaatcg tatgtgaatg ctggtcgcta tactgctgtc gattcgatac    4020
taacgccgcc atccagtgtc ggatctgtga gcaaaaggcc agcaaaggcc caggaaccgt    4080
aaaaaggccg cgttgctggc gtttttccat aggctccgcc cccctgacga gcatcacaaa    4140
aatcgacgct caagtcagag gtgacgaaac ccgacaggac tataaagata ccaggcgttt    4200 cccccctggaa gctccctcgt gcgctctcct gttccgaccc tgccgcttac cggatacctg    4260
tccgcctttc tcccttcggg aagcgtggcg ctttctcata gctcacgctg taggtatctc    4320
agttcggtgt aggtcgttcg ctccaagctg ggctgtgtgc acgaaccccc cgttcagccc    4380
gaccgctgcg ccttatccgg taactatcgt cttgagtcca acccgtaag acacgactta    4440 tcgccactgg cagcagccac tggtaacagg attagcagag cgaggtatgt aggcggtgct    4500
acagagttct tgaagtggtg gcctaactac ggctacacta agaacagt atttggtatc    4560 tgcgctctgc tgaagccagt taccttcgga aaaagagttg gtagctcttg atccggcaaa    4620
caaaccaccg ctggtagcgg tggttttttt gtttgcaagc agcagattac gcgcagaaaa    4680
aaaggatctc aagaagatcc tttgatcttt tctacggggt ctgacgctca gtggaacgaa    4740
aactcacgtt aagggatttt ggtcatgaga ttatcaaaaa ggatcttcac ctagatcctt    4800
tttaattaaa aatgaagatt taaatcaatc taaagtatat atgagtaaac ttggtctgac    4860
```

```
agttaccaat gcttaatcag tgaggcacct atctcagcga tctgtctatt tcgttcatcc    4920
atagttgcct gactcccgt cgtgtagata actacgatac gggagggctt accatctggc    4980
cccagtgctg caatgatacc gcgagatcca cgctcaccgg ctccagattt atcagcaata    5040
aaccagccgg ccggaagggc cgagcgcaga agtgggccgg ccactttatc cgcctccatc    5100
cagtctatta attgttgccg ggaagctaga gtaagtagtt cgccagttaa tagtttgcgc    5160
aacgttgttg ccattgctac aggcatcgtg gtgtcacgct cgtcgtttgg tatggcttca    5220
ttcagctccg gttcccaacg atcaaggcga gttacatgat ccccatgtt gtgcaaaaaa    5280 gcggttagct ccttcggtcc tccgatcgtt gtcagaagta agttggccgc agtgttatca    5340
ctcatggtta tggcagcact gcataattct cttactgtca tgccatccgt aagatgcttt    5400
tctgtgactg gtgagtactc aaccaagtca ttctgagaat agtgtatgcg cgaccgagt    5460 tgctcttgcc cggcgtcaat acgggataat accgcgccac atagcagaac tttaaaagtg    5520
ctcatcattg gaaaacgttc ttcggggcga aaactctcaa ggatcttacc gctgttgaga    5580
tccagttcga tgtaacccac tcgtgcaccc aactgatctt cagcatcttt tactttcacc    5640
agcgtttctg ggtgagcaaa aacaggaagg caaaatgccg caaaaaaggg aataagggcg    5700
acacggaaat gttgaatact catactcttc ctttttcaat attattgaag catttatcag    5760
ggttattgtc tcatgagcgg atacatattt gaatgtattt agaaaaataa acaaataggg    5820
gttccgcgca catttccccg aaaagtgcca cctgg                               5855

<210> SEQ ID NO 5
<211> LENGTH: 773
<212> TYPE: DNA
<213> ORGANISM: Artificial Sequence
<220> FEATURE:
<223> OTHER INFORMATION: Synthetic Oligonucleotide

<400> SEQUENCE: 5
gggtgaaagc caaccatctt tgtttcgggg aaccgtgctc gccccgtaaa gttaattttt     60
ttttcccgcg cagctttaat ctttcggcag agaaggcgtt ttcatcgtag cgtgggaaca    120
gaataatcag ttcatgtgct atacaggcac atggcagcag tcactatttt gcttttttaac   180 cttaaagtcg ttcatcaatc attaactgac caatcagatt ttttgcattt gccacttatc    240 taaaatact tttgtatctc gcagatacgt tcagtggttt ccaggacaac acccaaaaaa    300
aggtatcaat gccactaggc agtcggtttt attttggtc acccacgcaa agaagcaccc    360
acctctttta ggttttaagt tgtgggaaca gtaacaccgc ctagagcttc aggaaaaacc    420
agtacctgtg accgcaattc accatgatgc agaatgttaa tttaaacgag tgccaaatca    480
agatttcaac agacaaatca atcgatccat agttacccat tccagccttt tcgtcgtcga    540
gcctgcttca ttcctgcctc aggtgcataa cttttgcatga aagtccaga ttagggcaga    600 ttttgagttt aaaataggaa atataaacaa ataccgcg aaaaggttt gtttatagct      660 tttcgcctgg tgccgtacgg tataaataca tactctcctc ccccccctgg ttctcttttt    720
cttttgttac ttacatttta ccgttccgtc actcgcttca ctcaacaaca aaa            773

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide
```

```
<400> SEQUENCE: 6

Glu Asn Leu Tyr Phe Gln Gln Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(2)
<223> OTHER INFORMATION: Xaa is a hydrophobic amino acid
<220> FEATURE:
<221> NAME/KEY: MISC_FEATURE
<222> LOCATION: (5)..(6)
<223> OTHER INFORMATION: Xaa is a nonacidic amino acid

<400> SEQUENCE: 7

Xaa Xaa Pro Arg Xaa Xaa
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Arg or Lys

<400> SEQUENCE: 8

Arg Xaa Xaa Arg
1

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is a Ala, Val, Leu, Ile, Phe, Trp, or Tyr
<220> FEATURE:
<221> NAME/KEY: MISC_FEATURE
<222> LOCATION: (6)..(6)
<223> OTHER INFORMATION: Xaa is Gly, Ser, Glu, or Tyr
<220> FEATURE:
<221> NAME/KEY: MISC_FEATURE
<222> LOCATION: (7)..(10)
<223> OTHER INFORMATION: Xaa is any amino acid

<400> SEQUENCE: 9

Xaa Xaa Xaa Xaa Xaa Xaa Xaa Xaa Xaa Xaa
1               5                   10

<210> SEQ ID NO 10
<211> LENGTH: 5
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa is either Glu or Asp
<220> FEATURE:
<221> NAME/KEY: MISC_FEATURE
<222> LOCATION: (5)..(5)
<223> OTHER INFORMATION: Xaa is any amino acid except Proline

<400> SEQUENCE: 10

Ile Xaa Gly Arg Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Glu Asn Leu Tyr Phe Gln Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

Glu Asn Leu Tyr Phe Gln Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is either Gly or Ser

<400> SEQUENCE: 13

Glu Xaa Xaa Tyr Xaa Gln Xaa
1               5

<210> SEQ ID NO 14
<211> LENGTH: 93
<212> TYPE: DNA
<213> ORGANISM: Artificial Sequence
<220> FEATURE:
<223> OTHER INFORMATION: Synthetic Oligonucleotide

<400> SEQUENCE: 14
```

```
gtttctttgg acaagagaga ggctgaggct cgagaccatg cggccgcgtc ggccggtggt    60
gcttttgaag gaaaaccaat tccaaatcct ttg                                93
```

<210> SEQ ID NO 15
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 15

```
Val Ser Leu Asp Lys Arg Glu Ala Glu Ala Arg Asp His Ala Ala Ala
1               5                   10                  15

Val Ser Ala Gly Gly Ala Phe Glu Gly Lys Pro Ile Pro Asn Pro Leu
            20                  25                  30
```

<210> SEQ ID NO 16
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 16

```
gtttctttgg acaagagaga ggctga                                        26
```

<210> SEQ ID NO 17
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 17

```
agcctcagcc tctctcttgt ccaaagaaac                                    30
```

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18

```
Val Ser Leu Asp Glu Ser Glu Ala Glu Ala
1               5                   10
```

<210> SEQ ID NO 19
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 19

```
gccggtggtg cttttgaagg aaaaccaatt ccaaatcctt tg                      42
```

<210> SEQ ID NO 20
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 20

```
caaaggattt ggaattggtt ttccttcaaa agcaccac                                    38
```

<210> SEQ ID NO 21
<211> LENGTH: 14
<212> TYPE: PRT
<213> ORGANISM: Artificial Sequence
<220> FEATURE:
<223> OTHER INFORMATION: Synethic Peptide

<400> SEQUENCE: 21

```
Ala Gly Gly Ala Phe Glu Cys Glu Pro Ile Pro Asn Pro Leu
1               5                   10
```

<210> SEQ ID NO 22
<211> LENGTH: 388
<212> TYPE: PRT
<213> ORGANISM: Pichia pastoris

<400> SEQUENCE: 22

```
Met Arg Ser Asp Leu Thr Ser Ile Ile Val Phe Ala Val Ser Val Ile
1               5                   10                  15

Cys Val Leu Tyr Gly Pro Ser Gln Gln Leu Ser Ser Pro Lys Ile Asp
                20                  25                  30

Tyr Asp Pro Leu Thr Leu Arg Ser Leu Asp Leu Lys Thr Leu Glu Ala
            35                  40                  45

Pro Ser Gln Leu Ser Pro Gly Thr Val Glu Asp Asn Leu Arg Arg Gln
        50                  55                  60

Leu Glu Phe His Phe Pro Tyr Arg Ser Tyr Glu Pro Phe Pro Gln His
65                  70                  75                  80

Ile Trp Gln Thr Trp Lys Val Ser Pro Ser Asp Ser Ser Phe Pro Lys
                85                  90                  95

Asn Phe Lys Asp Leu Gly Glu Ser Trp Leu Gln Arg Ser Pro Asn Tyr
                100                 105                 110

Asp His Phe Val Ile Pro Asp Asp Ala Ala Trp Glu Leu Ile His His
            115                 120                 125

Glu Tyr Glu Arg Val Pro Glu Val Leu Glu Ala Phe His Leu Leu Pro
        130                 135                 140

Glu Pro Ile Leu Lys Ala Asp Phe Phe Arg Tyr Leu Ile Leu Phe Ala
145                 150                 155                 160

Arg Gly Gly Leu Tyr Ala Asp Met Asp Thr Met Leu Leu Lys Pro Ile
                165                 170                 175

Glu Ser Trp Leu Thr Phe Asn Glu Thr Ile Gly Gly Val Lys Asn Asn
                180                 185                 190

Ala Gly Leu Val Ile Gly Ile Glu Ala Asp Pro Asp Arg Pro Asp Trp
            195                 200                 205

His Asp Trp Tyr Ala Arg Arg Ile Gln Phe Cys Gln Trp Ala Ile Gln
        210                 215                 220

Ser Lys Arg Gly His Pro Ala Leu Arg Glu Leu Ile Val Arg Val Val
225                 230                 235                 240

Ser Thr Thr Leu Arg Lys Glu Lys Ser Gly Tyr Leu Asn Met Val Glu
                245                 250                 255

Gly Lys Asp Arg Gly Ser Asp Val Met Asp Trp Thr Gly Pro Gly Ile
                260                 265                 270

Phe Thr Asp Thr Leu Phe Asp Tyr Met Thr Asn Val Asn Thr Thr Gly
            275                 280                 285

His Ser Gly Gln Gly Ile Gly Ala Gly Ser Ala Tyr Tyr Asn Ala Leu
        290                 295                 300
```

Ser Leu Glu Glu Arg Asp Ala Leu Ser Ala Arg Pro Asn Gly Glu Met
305                 310                 315                 320

Leu Lys Glu Lys Val Pro Gly Lys Tyr Ala Gln Gln Val Val Leu Trp
            325                 330                 335

Glu Gln Phe Thr Asn Leu Arg Ser Pro Lys Leu Ile Asp Asp Ile Leu
        340                 345                 350

Ile Leu Pro Ile Thr Ser Phe Ser Pro Gly Ile Gly His Ser Gly Ala
    355                 360                 365

Gly Asp Leu Asn His His Leu Ala Tyr Ile Arg His Thr Phe Glu Gly
370                 375                 380

Ser Trp Lys Asp
385

<210> SEQ ID NO 23
<211> LENGTH: 1167
<212> TYPE: DNA
<213> ORGANISM: Artificial Sequence
<220> FEATURE:
<223> OTHER INFORMATION: Synthetic Oligonucleotide

<400> SEQUENCE: 23

```
atgagatcag atctaacatc cataatcgta ttcgccgttt ctgtcatttg cgttttgtac      60
ggaccctcac aacaattatc atctccaaaa atagactatg atccattgac gctccgatca     120
cttgatttga agactttgga agctccttca cagttgagtc caggcaccgt agaagataat     180
cttcgaagac aattggagtt tcattttcct taccgcagtt acgaaccttt tccccaacat     240
atttggcaaa cgtggaaagt ttctccctct gatagttcct ttccgaaaaa cttcaaagac     300
ttaggtgaaa gttggctgca aaggtcccca aattatgatc attttgtgat acccgatgat     360
gcagcatggg aacttattca ccatgaatac gaacgtgtac cagaagtctt ggaagctttc     420
cacctgctac cagagcccat tctaaaggcc gattttttca ggtatttgat tcttttttgcc     480
cgtggaggac tgtatgctga catggacact atgttattaa aaccaataga atcgtggctg     540
actttcaatg aaactattgg tggagtaaaa acaatgctgg gttggtcat tggtattgag      600
gctgatcctg atagacctga ttggcacgac tggtatgcta aaggataca attttgccaa      660
tgggcaattc agtccaaacg aggacaccca gcactgcgtg aactgattgt aagagttgtc     720
agcacgactt tacggaaaga gaaaagcggt tacttgaaca tggtgaagg aaaggatcgt      780
ggaagtgatg tgatggactg gacgggtcca ggaatattta cagacactct atttgattat     840
atgactaatg tcaatacaac aggccactca ggccaaggaa ttggagctgg ctcagcgtat    900
tacaatgcct tatcgttgga agaacgtgat gccctctctg cccgcccgaa cggagagatg     960
ttaaaagaga agtcccagg taaatatgca cagcaggttg ttttatggga acaatttacc    1020
aacctgcgct cccccaaatt aatcgacgat attcttattc ttccgatcac cagcttcagt    1080
ccagggattg ccacagtgg agctggagat ttgaaccatc accttgcata tattaggcat    1140
acatttgaag gaagttggaa ggactaa                                       1167
```

<210> SEQ ID NO 24
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 24

```
gcgcgcggtc tcgggct                                                    17

<210> SEQ ID NO 25
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 25
gccgggagac cgcgcgc                                                    17

<210> SEQ ID NO 26
<211> LENGTH: 216
<212> TYPE: DNA
<213> ORGANISM: Artificial Sequence
<220> FEATURE:
<223> OTHER INFORMATION: Synthetic Oligonucleotide

<400> SEQUENCE: 26
aaggaggagg gtgtttcttt ggacaagaga gaggctgagg ctcgagacca tgcggccgcg     60
gtctcggccg gtggtgcttt tgaaggaaaa ccaattccaa atcctttgtt gggattggat    120
tctacttctg ccaaatcatc tttcatttca accaccacca ctgatttgac ttcaatcaac    180
acttctgctt actctactgg atctatttca actgtt                              216

<210> SEQ ID NO 27
<211> LENGTH: 72
<212> TYPE: PRT
<213> ORGANISM: Artificial Sequence
<220> FEATURE:
<223> OTHER INFORMATION: Synthetic Peptide

<400> SEQUENCE: 27

Lys Glu Glu Gly Val Ser Leu Asp Lys Arg Glu Ala Glu Ala Arg Asp
1               5                   10                  15

His Ala Ala Ala Val Ser Ala Gly Gly Ala Phe Glu Gly Lys Pro Ile
            20                  25                  30

Pro Asn Pro Leu Leu Gly Leu Asp Ser Thr Ser Ala Lys Ser Ser Phe
        35                  40                  45

Ile Ser Thr Thr Thr Thr Asp Leu Thr Ser Ile Asn Thr Ser Ala Tyr
    50                  55                  60

Ser Thr Gly Ser Ile Ser Thr Val
65                  70
```

PICHIA PASTORIS SURFACE DISPLAY SYSTEM

CROSS REFERENCE TO RELATED APPLICATION

This application claims the benefit of priority of U.S. Provisional Application No. 61/920,182, filed Dec. 23, 2013, the entire contents of which are incorporated herein by reference.

INCORPORATION BY REFERENCE OF SEQUENCE LISTING

The Sequence Listing in an ASCII text file, named 31551_Sequence_Listing.txt of 43 KB, created on Jun. 22, 2016, and submitted to the United States Patent and Trademark Office via EFS-Web, is incorporated herein by reference.

BACKGROUND ART

*Pichia pastoris* is a highly successful system for production of a wide variety of recombinant proteins. Several factors have contributed to its rapid acceptance, including: (1) a promoter derived from the alcohol oxidase I (AOX1) gene of *P. pastoris* that is uniquely suited for the controlled expression of foreign genes; (2) the similarity of techniques needed for the molecular genetic manipulation of *P. pastoris* to those of *Saccharomyces cerevisiae*; and (3) the strong preference of *P. pastoris* for respiratory growth, a physiological trait that facilitates its culturing at high-cell densities relative to fermentative yeasts.

As a yeast, *P. pastoris* is a single-celled microorganism that is easy to manipulate and culture. However, it is also a eukaryote and capable of many of the posttranslational modifications performed by higher eukaryotic cells such as proteolytic processing, folding, disulfide bond formation and glycosylation. Thus, many proteins that would end up as inactive inclusion bodies in bacterial systems are produced as biologically active molecules in *P. pastoris*. The *P. pastoris* system is also generally regarded as being faster, easier, and less expensive to use than expression systems derived from higher eukaryotes such as insect and mammalian tissue culture cell systems and usually gives higher expression levels.

*P. pastoris* has the potential of performing many of the posttranslational modifications typically associated with higher eukaryotes. These include processing of signal sequences (both pre- and prepro-type), folding, disulfide bridge formation, and both O- and N-linked glycosylation. Glycosylation of secreted foreign (higher) eukaryotic proteins by *P. pastoris* and other fungi can be problematic. In mammals, O-linked oligosaccharides are composed of a variety of sugars including N-acetylgalactosamine, galactose and sialic acid. In contrast, lower eukaryotes, including *P. pastoris*, may add O-oligosaccharides solely composed of mannose (Man) residues.

N-glycosylation in *P. pastoris* is also different than in higher eukaryotes. As in all eukaryotes, it begins in the ER with the transfer of a lipid-linked oligosaccharide unit, Glc3Man9GlcNAc2 (Glc=glucose; GlcNAc=N-acetylglucosamine), to asparagine at the recognition sequence Asn-X-Ser/Thr. This oligosaccharide core unit is subsequently trimmed to Man8GlcNAc2. It is at this point that lower and higher eukaryotic glycosylation patterns begin to differ. The mammalian Golgi apparatus performs a series of trimming and addition reactions that generate oligosaccharides composed of either Man5-6GlcNAc2 (high mannose type), a mixture of several different sugars (complex type) or a combination of both (hybrid type). Two distinct patterns of N-glycosylation have been observed on foreign proteins secreted by *P. pastoris*. Some proteins are secreted with carbohydrate structures similar in size and structure to the core unit (Man8-11GlcNAc2). Other foreign proteins secreted from *P. pastoris* receive much more carbohydrate and appear to be hyperglycosylated.

N-linked high mannose oligosaccharides added to proteins by yeasts represent a problem in the use of foreign secreted proteins by the pharmaceutical industry. For example, they can be exceedingly antigenic when introduced intravenously into mammals and furthermore may cause rapid clearance of the protein from the blood by the liver.

In an attempt to modify the N-glycosylation pathway of *Pichia pastoris*, a strain (hereinafter referred to as "M5-Blast") was created, as described in Jacobs et al., 2009, *Nature Protocols* 4:58-70. The M5-Blast strain is a modification of the *P. pastoris* GS115 strain wherein the endogenous mannosyltransferase gene OCH1 is disrupted by the introduction of a cassette comprising an α-1,2 mannosidase gene. However, the M5-Blast strain is subject to genomic rearrangements that regenerate the endogenous OCH1 gene and in parallel remove the α-1,2 mannosidase gene after rounds of freezing and thawing, growth under various temperatures and conditions, and from subsequent transformations with other plasmids to introduce exogenous genes.

Novel *Pichia pastoris* strains with substantially homogeneous N-glycans displayed on cell surface proteins have been constructed (e.g., "SuperMan5"). The novel *Pichia pastoris* strains are genetically engineered to include a mutant OCH1 allele that is transcribed into an mRNA coding for a mutant OCH1 gene product (e.g., α-1,6-mannosyltransferase, or "OCH1 protein"). The mutant OCH1 protein contains a catalytic domain substantially identical to that of the wild type OCH1 protein, but has an N-terminal sequence that alters the localization of the OCH1 protein to or in the Golgi apparatus. The novel *Pichia pastoris* strains do not include any other OCH1 allele that produces an mRNA coding for a functional OCH1 protein. Such strains are robust, stable, and transformable, and the mutant OCH1 allele and the associated phenotype (e.g., ability to produce substantially homogeneous N-glycans) are maintained for generations, after rounds of freezing and thawing, and after subsequent transformations. Such engineered *Pichia pastoris* strains (e.g., SuperMan5) are described in PCT/US13/66335 (published as WO2014/066479A1), the specification of which is incorporated herein in its entirety by reference.

Yeast surface display is a platform used for the engineering, screening and isolation of a variety of proteins, particularly recombinant proteins. Notably yeast surface display has evolved as a tool for engineering and isolation of antibodies and antibody fragments. Without wishing to limit the present invention to any theory or mechanism, it is believed that an advantage of the yeast display tool is that it uses an expression and processing pathway similar to that of higher eukaryotes. Proteins are folded in the ER, where they benefit from the presence of chaperones, foldases, and of quality control mechanisms and can have eukaryotic post-translational modifications. Additional advantages may include the possibility to rapidly and quantitatively screen antibody affinity and display level through fluorescent-activated cell sorting (FACS).

SUMMARY OF THE DISCLOSURE

The present invention features novel *Pichia pastoris* display systems, e.g., display systems featuring the *Pichia pastoris* strains (e.g., SuperMan5) with substantially homogeneous N-glycans displayed on cell surface proteins.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1 shows the vector map for the vector pJGG-display.

FIG. 2 shows the vector map for the vector pJAG-display.

FIG. 3A and FIG. 3B show detailed views of the Bsa I digestion sites for insertion of an open reading frame (ORF) (of the recombinant protein of interest) into the vector pJGG-display/pJAG-display.

FIG. 7 shows fluorescence microscopy of AOX1 constructs (Green: anti-V5; red: ConA).

FIG. 8 shows fluorescence microscopy of GAP constructs (Green: anti-V5; red: ConA).

FIG. 9 shows fluorescence microscopy of UP constructs (Green: anti-V5; red: ConA).

Figure 4:
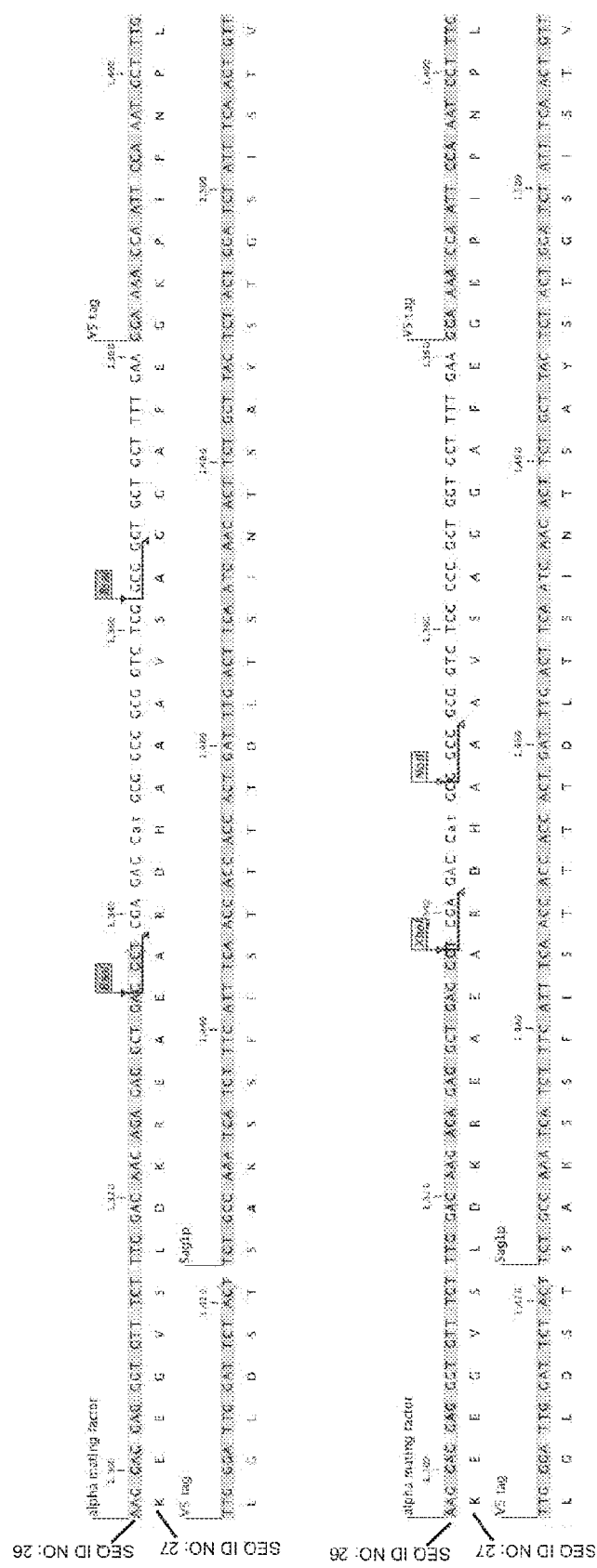
FIG. 4 shows the cloning region for insertion of protein(s) of interest. In frame insertion into the fusion protein can be accomplished using either flanking Bsa I sites or using either single or combined Xho I and Not I sites in the stuffer region of the vectors (stuffer region referring to a short fragment containing Bsa I restriction sites).

Table 1 lists the DNA sequence (SEQ ID NO: 1) of the OCH1 locus in a SuperMan5 strain.

Table 2A lists the amino acid sequence (SEQ ID NO: 2) for the wild type OCH1 protein in *Pichia pastoris*. Table 2B lists the amino acid sequence (SEQ ID NO: 22) for a mutant OCH1 protein in a *Pichia pastoris* SuperMan5 strain.

Table 3 lists the DNA sequence (SEQ ID NO: 3) for the vector pJGG-display.

Table 4 lists the DNA sequence (SEQ ID NO: 4) for the vector pJAG-display.

Table 5 lists the DNA sequence (SEQ ID NO: 5) for the UP promoter of pJUG-display.

DETAILED DESCRIPTION

The present invention features novel *Pichia pastoris* cell surface display systems. The systems comprise engineered *Pichia pastoris* strains, e.g., those such as SuperMan5 described in PCT/US13/66335 (see below, e.g., *Pichia pastoris* comprising the OCH1 locus of SEQ ID NO: 1), with substantially homogeneous N-glycans displayed on cell surface proteins. The present invention also features vectors designed to direct secretion and covalent attachment of recombinant proteins to the cell wall of said engineered *Pichia pastoris*. Various methods can be used to identify and enrich the engineered *Pichia pastoris* cells expressing the recombinant protein on their cell surfaces. The engineered *Pichia pastoris* cells (and vectors) described herein may be used as tools for cell surface display. As an example, protein libraries can be expressed on the cell wall of the engineered *Pichia* and panning or sorting techniques may be used to isolate clones with specific binding properties to a probe of interest.

Engineered *Pichia pastoris*

The surface display systems of the present invention feature engineered strains of *Pichia pastoris* that produce a homogenous (or nearly homogenous) population of N-glycans on their cell surface proteins ("cell surface proteins" refers to both the normally present cell surface proteins of the engineered *Pichia pastoris* strain and the recombinant protein(s) that the *Pichia pastoris* strain is engineered to display). The N-glycans may be, for example, mannose-3 N-glycans, mannose-5 N-glycans, or mannose-8 N-glcyans. In some embodiments, the population of N-glycans is more than about 95% homogenous. In some embodiments, the population of N-glycans is more than about 90% homogenous. In some embodiments, the population of N-glycans is more than about 80% homogenous. In some embodiments, the population of N-glycans is more than about 70% homogenous.

The engineered *Pichia pastoris* strain provides an environment that allows for more and/or better interaction between the recombinant protein displayed on the engineered *Pichia pastoris* cell surface and a binding partner as compared to wild type *Pichia pastoris* (and/or *S. cerevisiae*). The complement of glycoproteins on the cell surface of these engineered *Pichia pastoris* cells will have N-glycans of shorter length (e.g., about 10% shorter, 20% shorter, 50% shorter, etc.) compared to the N-glycans of wild-type *Pichia pastoris*. This will reduce the glycocalyx layer found at the outside surface of the cell wall. Thus, the displayed protein will "stand out" better among the cell wall components in the engineered *Pichia*. For example, the recombinant protein that is displayed on the surface of the engineered *Pichia pastoris* strain may be more accessible as compared to wild type *Pichia pastoris* (and/or *S. cerevisiae*).

Binding assays may help show the increased accessibility of the recombinant protein (on the engineered *Pichia pastoris*). For example, it may be possible to compare the amount of binding of binding partners (say, for example, protein A on the surface of the *Pichia pastoris* and protein B, which is introduced to the *Pichia pastoris* in a binding assay) when displayed on the engineered *Pichia pastoris* or on wild type *Pichia pastoris*. In some embodiments, there is between about 5-15% more binding (of the binding partners) when the recombinant protein is displayed on the engineered *Pichia pastoris* as compared to wild type *Pichia pastoris*. In some embodiments, there is between about 15-25% more binding (of the binding partners) when the recombinant protein is displayed on the engineered *Pichia pastoris* as compared to wild type *Pichia pastoris*. In some embodiments, there is between about 25-50% more binding (of the binding partners) when the recombinant protein is displayed on the engineered *Pichia pastoris* as compared to wild type *Pichia pastoris*. In some embodiments, there is between about 50-75% more binding (of the binding partners) when the recombinant protein is displayed on the engineered *Pichia pastoris* as compared to wild type *Pichia pastoris*. In some embodiments, there is more than about 75% more binding (of the binding partners) when the recombinant protein is displayed on the engineered *Pichia pastoris* as compared to wild type *Pichia pastoris*.

This enhanced interaction or increased accessibility may be achieved due to various reasons, e.g., thinner and/or shorter glycocalyx, reduced sugar density, etc. Or, there may also be epitopes on the displayed recombinant protein that are not accessible when using wild type *Pichia* with wild type cell wall glycan composition.

In some embodiments, the engineered *Pichia pastoris* strain may have fewer sugar moieties than wild type *Pichia pastoris* (and/or *S. cerevisiae*), e.g., about 5% fewer sugar moieties, between about 5-10% fewer sugar moieties, between about 10-25% fewer sugar moieties, between about 25-50% fewer sugar moieties, between about 50-75% fewer sugar moieties, more than 75% fewer sugar moieties, etc. In some embodiments, the engineered *Pichia pastoris* strain may have a population of N-glycans on its surface of that is less dense than the population of N-glycans on the surface of wild type *Pichia pastoris* (and/or *S. cerevisiae*), e.g., about 5% less dense, between about 5-10% less dense, between about 10-25% less dense, between about 25-50% less dense, between about 50-75% less dense, more than 75% less dense, etc. In some embodiments, the engineered *Pichia pastoris* strain may have an overall shortened population of N-glycans compared to wild type *Pichia pastoris* (and/or *S. cerevisiae*).

In some embodiments, the N-glycans of the engineered *Pichia pastoris* strain are between about 5-10% shorter than the N-glycans of wild type *Pichia pastoris*. In some embodiments, the N-glycans of the engineered *Pichia pastoris* strain are between about 10-20% shorter than the N-glycans of wild type *Pichia pastoris*. In some embodiments, the N-glycans of the engineered *Pichia pastoris* strain are between about 20-30% shorter than the N-glycans of wild type *Pichia pastoris*. In some embodiments, the N-glycans of the engineered *Pichia pastoris* strain are between about 30-50% shorter than the N-glycans of wild type *Pichia pastoris*. In some embodiments, the N-glycans of the engineered *Pichia pastoris* strain are between about 50-75% shorter than the N-glycans of wild type *Pichia pastoris*. In some embodiments, the N-glycans of the engineered *Pichia pastoris* strain are more than about 75% shorter than the N-glycans of wild type *Pichia pastoris*.

The engineered *Pichia pastoris* strains may be made competent for transformation of a vector (e.g., as described below) encoding a recombinant protein for cell surface display.

For reference, the engineered *Pichia pastoris* strain SuperMan5, which produces substantially homogenous N-glycans (e.g., Man5GlcNAc2) on its cell surface proteins, may comprise a mutant OCH1 allele that is transcribed into a mRNA coding for a mutant OCH1 protein that comprises a catalytic domain substantially identical with that of the wild type OCH1 protein, and an N-terminal sequence that alters the Golgi localization of the mutant OCH1 protein as compared to the wild type OCH1 protein. The C-terminal fragment of the mutant OCH1 protein (which comprises the catalytic domain) may be at least 95% identical with amino acids 45-404 of SEQ ID NO: 2 (with SEQ ID NO: 2 representing the wild type amino acid sequence of the OCH1 protein, and amino acids 45-404 representing the C-terminal fragment which comprises the catalytic domain of the wild type OCH1 protein). In most embodiments, the catalytic domain of the mutant OCH1 protein does not differ from the wild type domain by more than 10 amino acids, 8 amino acids, 5 amino acids, 3 amino acids, or 2 amino acids. In specific embodiments, the catalytic domain of the mutant OCH1 protein is identical with that of the wild type OCH1 protein. In some embodiments, the mutant OCH1 protein lacks an N-terminal sequence for targeting the mutant OCH1 protein to the Golgi apparatus. In some embodiments, the mutant OCH1 protein lacks a membrane anchor domain at the N-terminal region, e.g., a result of deleted portion of an N-terminal portion of the OCH1 wild type protein. The wild type OCH1 protein has a short cytoplasmic tail (Met1 to Tyr21, or Ala2 to Tyr21), a membrane anchor domain (Phe22 to Ser44), and a stem region. The deleted portion may comprise one or more amino acids of the membrane anchor domain of the wild type OCH1 protein, and/or one or more amino acids of the cytoplasmic tail of the wild type OCH1 protein. In specific embodiments, the deleted portion includes at least 15, 16, 17, 18, 19, 20, 21, 22, 23, 24 or 25 amino acids of the N-terminal sequence of the wild type OCH1 protein (beginning from Met at position 1). In some embodiments, the mutant OCH1 protein is encoded by the nucleotide sequence of SEQ ID NO: 23, and comprises the sequence as set forth in SEQ ID NO: 22.

The engineered *Pichia pastoris* strain, e.g., SuperMan5, may further comprise a nucleic acid coding for and expressing an α-1,2-mannosidase or a functional fragment thereof. The nucleic acid coding for and expressing said α-1,2-mannosidase (or the functional fragment thereof) may be integrated at the OCH1 locus of the strain. The engineered *Pichia pastoris* strain, e.g., SuperMan5, may further comprise a nucleic acid coding for and expressing a recombinant protein, e.g., for display on the cell surface.

The engineered *Pichia pastoris* strain, e.g., SuperMan5, may further comprise a nucleic acid coding for and expressing an mannosidase-II or a functional fragment thereof. The engineered *Pichia pastoris* strain would now produce substantially Man3GlcNAc2 glycoproteins. The engineered *Pichia pastoris* strain, e.g., SuperMan3, may further comprise a nucleic acid coding for and expressing a recombinant protein, e.g., for display on the cell surface.

Vectors for Cell Surface Display

The display systems of the present invention may comprise an engineered DNA vector coding for and expressing a recombinant protein adapted to be displayed on the surface of the engineered *Pichia pastoris* strain. As an example, the engineered DNA vector may comprise pJGG-display (SEQ ID NO: 3). Or, the engineered DNA vector may comprise pJAG-display (SEQ ID NO: 4). Or, the engineered DNA vector may comprise pJUG-display (SEQ ID NO: 5). The engineered DNA vector is not limited to pJGG-display, pJAG-display, and pJUG-display. Any appropriate DNA vector may be incorporated.

The engineered DNA vector is adapted to be inserted into a *Pichia pastoris* strain, e.g., SuperMan5. The vector may be inserted via any appropriate insertion means, e.g., transformation, electroporation, etc.

Figure 10:
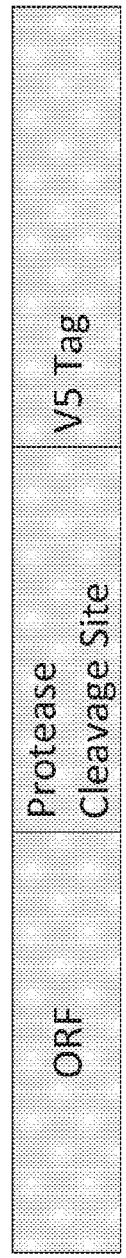
FIG. 10 shows a schematic view of an example wherein a protease cleavage site is posited between the ORF/recombinant protein of interest and the V5 tag.

The vector may encode a protease cleavage site. For example, the protease cleavage site may be positioned between the recombinant protein ORF and the V5 tag (see FIG. 10), or at another location, e.g., at or near the N-terminal region of the recombinant protein, etc. Cleavage can occur when the protease cleavage site is digested by its corresponding protease. In an embodiment where the protease cleavage site is positioned between the sequence for the recombinant protein of interest and the V5 tag, cleavage via the protease allows the V5 tag, or other relevant tag (e.g. Flag-tag), to be eliminated from the recombinant protein of interest when desired, leaving the recombinant protein of interest displayed on the cell surface. Protease cleavage sites and their corresponding proteases are well known to one of ordinary skill in the art. For example, the protease may comprise the tobacco etch virus (TEV) protease, thrombin, ficin, factor Xa serine endoproteinase, (see below), pepsin, papain, neutrase, methionine aminopeptidase, matrix metalloprotease (MMP), leucine aminopeptidase, endoproteinase Arg-C murine submaxillary gland, HIV-1 protease, furin, granzyme A, granzyme B, and/or the like.

The appropriate protease (and protease cleavage site) may be selected based on the sequence of the recombinant protein of interest (to avoid non-specific cleavage). For example, the sequence of the recombinant protein of interest (and optionally other linked peptides, e.g., the V5 tag, etc.) may be compared with the protease cleavage site of the protease to ensure that the recombinant protein of interest does not have the protease cleavage site within its sequence so as to prevent cleavage at an undesired site.

The protease may be encoded and expressed from the vector (or a separate vector) and under the control of a separate second promoter (the second promoter being different from the promoter controlling expression fo the recombinant protein). The second promoter may be an inducible promoter to control expression of the protease. Any appropriate promoter may be utilized. Promoters for such purposes are well known to one of ordinary skill in the art. In some embodiments, the second promoter comprises the formaldehyde dehydrogenase (FLD) promoter, alcohol oxidase (AOX1), UP promoter or any other appropriate promoter.

Again, in some embodiments, the protease is encoded for in a vector, e.g., the vector of the recombinant protein or a separate vector. In some embodiments, the protease is supplied in the medium.

As an example, the cleavage site sequence of ENLYFQQS (SEQ ID NO: 6) may be engineered into the fusion protein and when one wanted to not display the protein (e.g., instead have the protein cleaved and secreted into the medium), the Tobacco Etch Virus (TEV) protease gene could be transformed into the host strain in a separate transformation and under a separate regulatable/inducible promoter (e.g., AOX1, FLD). The TEV protease can then be produced upon induction, and then can cleave the protein at the appropriate site (which depending on where the cleavage site is located may result in the release from the cell surface of the displayed protein).

Non-limiting examples of protease recognition sites include the following amino acid sequences: (1) A-B-Pro-Arg-||-X-Y where A and B are hydrophobic amino acids and X and Y are nonacidic amino acids (SEQ ID NO: 7) (thrombin is the corresponding protease); (2) Gly-Arg-||-Gly (thrombin is the corresponding protease); (3) Arg-X-||-Y-Arg where X is any amino acid and Y is Arg or Lys (SEQ ID NO: 8) (Ficin is the corresponding protease); (4) Xaa-Xaa-Xaa-Xaa-Yaa-Zaa-||-Xaa-Xaa-Xaa-Xaa where Xaa is any amino acid and Yaa is a Ala, Val, Leu, Ile, Phe, Trp, or Tyr and Zaa is Gly, Ser, Glu, or Tyr (SEQ ID NO: 9) (Ficin the corresponding protease); (5) Ile-Glu (or Asp)-Gly-Arg||-X (X is not Proline) (SEQ ID NO: 10) (Factor Xa is the corresponding protease); (6) ENLYFQQS (SEQ ID NO: 6) (TEV is corresponding protease); (7) ENLYFQG (SEQ ID NO: 11) (TEV is corresponding protease); (8) ENLYFQS (SEQ ID NO: 12) (TEV is corresponding protease); (9) EXaaX-aaYXQ(G/S) where Xaa is any amino acid (SEQ ID NO: 13) (TEV is corresponding protease).

The recombinant protein may be expressed (and displayed) via standard expression protocols. A non-limiting example of a standard expression protocol includes methanol induction.

Also featured herein are the following *Pichia pastoris* strains of Table B (optionally made competent):

TABLE B

| | Strain | Mutations | Origin |
|---|---|---|---|
| (a) | SuperMan5 | (HIS4+, Mut+, och1−, blastocidin res, mannosidase 1) | Derived from GSMan5 with added deletion in OCH1 |
| (b) | SuperMan5 (pJGG-display) | (HIS4+, Mut+, och1−, blastocidin res, mannosidase 1) | SuperMan5 with pJGG-display |
| (c) | SuperMan5 (pJAG-display) | (HIS4+, Mut+, och1−, blastocidin res, mannosidase 1) | SuperMan5 with pJAG-display |
| (d) | SuperMan5 (pJUG-display) | (HIS4+, Mut+, och1−, blastocidin res, mannosidase 1) | SuperMan5 with pJUG-display |
| (e) | SuperMan5 (HIS−) | (HIS4−, Mut+, och1−, blastocidin res, mannosidase 1) | SuperMan5 with HIS− |
| (f) | SuperMan5 (Mut-s) | (Mut-s, och1−, aox1-blastocidin res, mannosidase 1) | Same as KM71H, slow methanol utilization with aox1 KO |
| (g) | SuperMan5 (pep4−) | (pep4−, och1−, blastocidin res, mannosidase 1) | Same as SMD1168, protease A KO |
| (h) | SuperMan5 (prb1−) | (prb1−, och1−, blastocidin res, mannosidase 1) | Same as SMD1163, protease B KO |
| (i) | SuperMan5 (prb1−/pep4−) | (pep4−, prb1−, och1−, blastocidin res, mannosidase 1) | Double protease KO |
| (j) | SuperMan5 (pep4−/sub2−) | (pep4−, sub2−, och1−, blastocidin res, mannosidase 1) | KO of protease A and subtilisin2 |

The pJAG-display, pJGG-display, and pJUG-display vectors may contain one or several of the following elements (or appropriate variations thereof): (a) *Pichia* codon optimized α mating factor pre-, pro-leader sequence from *S. cerevisiae* for targeting of the encoded protein to the *Pichia* secretory pathway; (b) *Pichia* codon optimized SAG1 gene fragment from *S. cerevisiae* (this fragment directs GPI-anchor addition and subsequent covalent attachment to the cell wall of the protein(s) encoded by its fusion to a gene or library of interest); (c) V5 epitope tag for detection and normalization of the surface expressed protein; (d) Dominant G418, or other, selection marker for transformation of *Pichia*; (e) pUC backbone for replication and ampicillin selection in *E. coli*; (f) pJAG-display utilizes the *Pichia* AOX1 promoter for methanol-inducible expression of the SAG1 gene fusion, pJGG-display contains the strong, constitutive *Pichia* GAP promoter, or the pJUG-display contains the UP promoter (see Table 5).

Sag1p is the α-agglutinin molecule present on *S. cerevisiae* α cells responsible for mating type-specific agglutination (Zhao et al., J Bacteriol 183(9):2874-80, 2001). Its C-terminal domain is highly glycosylated and contains a hydrophobic tail that directs GPI-anchor addition in the endoplasmic reticulum. After passage through the secretory pathway and arrival at the cell surface, a transglycosylation reaction covalently transfers Sag1p from the lipid bilayer of the plasma membrane to β-glucan in the cell wall. The dynamics of cell wall growth result in exposure of Sag1p at the cell wall surface, where it can interact with its agglutination partner on *S. cerevisiae* αcells. Fusion with the last 320 amino acids of Sag1p is sufficient to target and covalently attach proteins to the cell wall of *Pichia* (Ryckaert et al., Glycobiol 18:137-144, 2008). Because the GPI-anchor signal resides in its C-terminal hydrophobic domain, fusion partners are attached to the N-terminus of the Sag1p fragment. When targeted to the secretory pathway as Sag1p fusion proteins, antibody fragments and lectins have been shown to express functional binding on the cell surface of *Pichia* (Ryckaert et al. 2008; Ryckaert et al., J Biotechnol. 145(2):93-8, 2010, Epub Oct. 25, 2009).

EXAMPLE 1

Experimental Procedure

The following example describes construction of a *Pichia* SuperMan5 strain expressing a recombinant protein for cell surface display.

Design PCR primers to amplify insert or library for in frame fusion with both the α mating factor leader and SAG1 fragment. Clone or assemble PCR product(s) into pJAG-display and/or pJGG-display and/or pJUG-display. Transform into *E. coli* and select on LB-Amp plates. For single insert constructs, sequence verify gene fusions. For libraries, verify insertion frequency into vector(s) by PCR, sequence verify small number of clonal isolates. Amplify and prepare DNA from *E. coli*. Linearize DNA with unique restriction site in the *Pichia* promoter or terminator. Transform linear DNA into competent *Pichia* SuperMan5 cells and select on YPD-G418 plates. For single insert transformations, verify genomic integration by PCR. For libraries, verify genomic integration by PCR for a small number of clonal isolates. Verify expression of fusion protein using V5 epitope tag. Perform binding assays and/or clonal enrichment, using V5 tag to normalize for expression variability and cell size.

As shown in FIG. 3A, Bsa/digestion may be used to create a seamless junction at the second Ste13p cleavage site of the α mating factor leader. Bsa I is a Type IIS restriction enzyme, where the 5' overhang after digestion is context dependent. By designing these sticky ends to be mismatching, cloning into Bsa I digested vectors is directional. In addition, since all four 5' overhangs on the vector and a properly designed insert are non-palindromic, neither vector nor insert multimerization can occur. This approach also allows other Type IIS enzymes to be used to generate the sticky ends on the insert fragment if it contains internal Bsa I sites. As shown in FIG. 3B, the addition of 18 base extensions onto forward and reverse PCR primers can be used to generate in frame Bsa I sites on a specific insert or library. By changing the lower case g/c pairs to c/g pairs, the specificity can be altered to use BsmB I to prepare the insert.

EXAMPLE 2

Experimental Procedure

The following example describes insertion of a synthetic DNA fragment (V5 epitope tagged) into a *Pichia* SuperMan5 strain.

The synthetic DNA fragment was cloned into a variety of expression vectors containing 3 different promoters and 3 different drug selection markers using the BsmB I sites encoded in the ends of the fragment. In all cases, targeting to the secretory pathway is directed by the *S. cerevisiae* alpha mating factor encoded in the vectors. The synthetic DNA was designed so that vectors without an insert have the Sag1p fragment in frame with the alpha mating factor and should produce V5-tagged material on the cell surface. Vectors for inducible expression were created using the *Pichia pastoris* AOX1 promoter and vectors for constitutive expression created using both the *Pichia* GAP promoter (and an additional promoter under stud). For all vectors, cloning into the expression cassette is identical, as diagrammed in FIG. 4.

Table A details the promoter/drug selection marker combinations that were constructed with the above insert. Inserts into the vectors were sequenced in both directions and verified as correct.

TABLE A

| Vector | Promoter | Linearization Enzyme | Drug Selection |
|---|---|---|---|
| pJAGs1-V5-SAG1 | *P. pastoris* AOX1 | Pme I | G418 |
| pJANs1-V5-SAG1 | *P. pastoris* AOX1 | Pme I | nourseothricin |
| pJAZs1-V5-SAG1 | *P. pastoris* AOX1 | Pme I | Zeocin |
| pGGs1-V5-SAG1 | *P. pastoris* GAP | Avr II | G418 |
| pJGZs1-V5-SAG1 | *P. pastoris* GAP | Avr II | Zeocin |
| pJUGs1-V5-SAG1 | *P. pastoris* UP | Bsu36 I | G418 |

One construct for each promoter was linearized with the appropriate restriction enzyme and transformed into the SuperMan5 his+ and BG10 wild-type strains. Transformants were selected using the appropriate drug on YPD plates.

Individual colonies were picked and patched to YPD plates. For initial analysis, patched cells were taken directly from YPD plates and stained for cell surface V5 epitopes and counter-stained with ConA for general cell surface mannose. V5 detection was performed with FITC-labeled anti-V5 (Abcam: http://www.abcam.com/V5-tag-antibody-FITC-ab1209.html) and mannose labeling with AlexaFluor647-labeled ConA (Molecular Probes: www.lifetechnologies.com).

Briefly, cells were blocked in RIPA buffer containing azide and Vector Labs' Carbo-Free blocking solution for >1 hour, followed by incubation with anti-V5 and ConA for >1 hour. Both incubations were performed at 4-8° C. After binding, cells were washed 4 times with 25 mM Tris, pH 7.5. Stained cells were analyzed on an Accuri C6 flow cytometer. The flow cytometer has 4 color detection, in addition to forward and side scatter analysis. Anti-V5 is detected using 488 nm laser excitation with a 530±15 nm emission filter. ConA is detected using 640 nm laser excitation with a 675±12.5 nm emission filter. There was no apparent bleed-through between the two detection channels.

Figure 5:
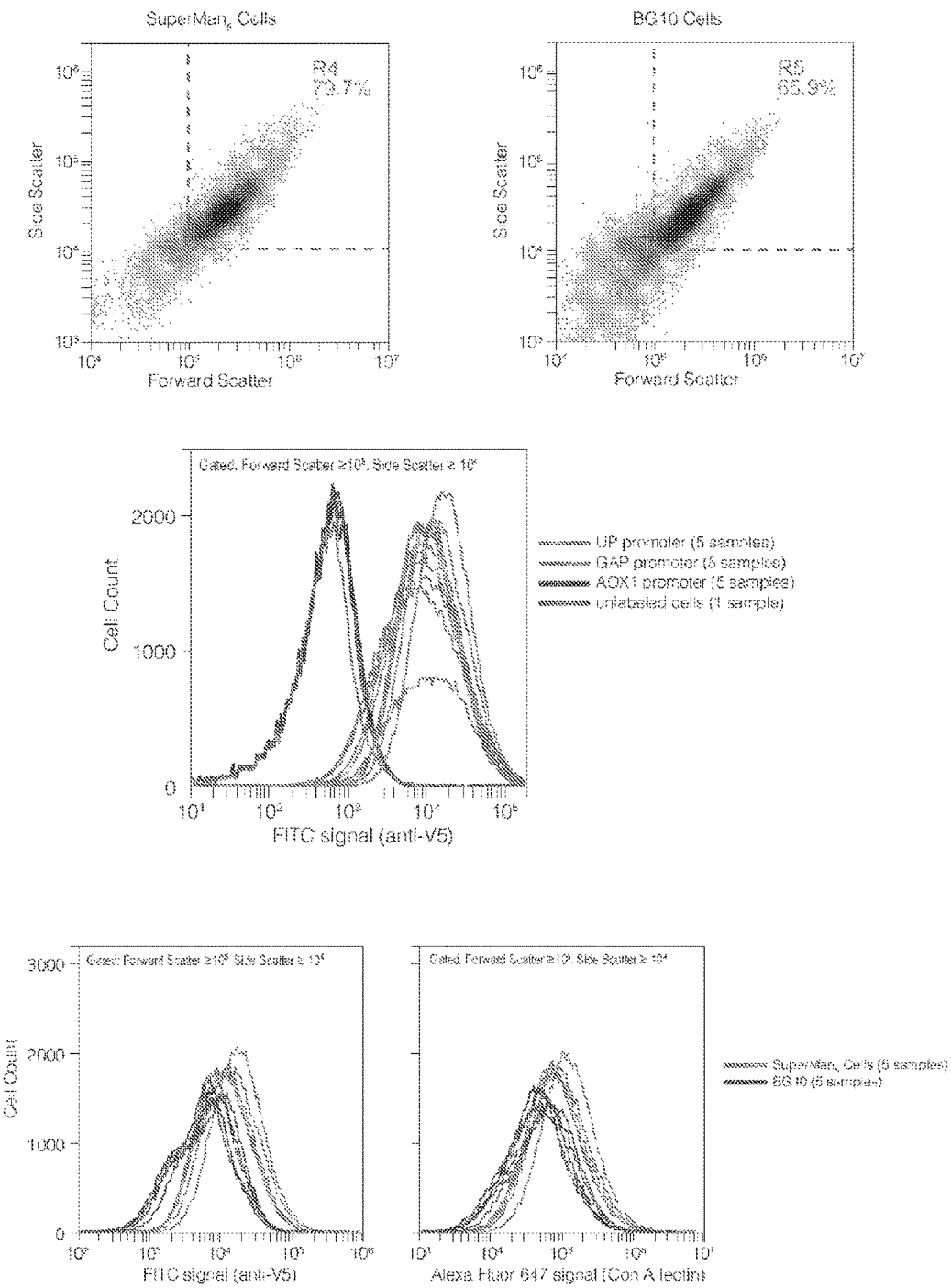
FIG. 5 shows flow cytometry analysis of cells grown on YPD plates.

FIG. 5 shows panels in which 5 individual isolates from each transformation were analyzed. The top two panels show forward/side scatter plots of SuperMan5 and BG10 cells. In general, SuperMan5 cells were slightly larger based on forward/side scatter plotting. Flow cytometry events were gated for forward scatter $\geq 10^5$ and side scatter $\geq 10^4$ and fluorescence signals plotted. The middle panel shows FITC signals for SuperMan5 cells for each of the 3 promoters. The 5 individual isolates of the GAP and UP promoter constructs showed almost identical FITC signal, approximately 2 orders of magnitude greater than unlabeled cells. The 5 individual isolates of the AOX1 promoter constructs were almost indistinguishable from unlabeled cells (note that cells in these experiments were grown using glucose as the carbon source). In the bottom 2 panels, the ConA and anti-V5 signals were compared for the UP promoter constructs in both SuperMan5 and BG10 wild-type cells. The ratio of ConA to anti-V5 signal is essentially identical between the two strains and the slight difference in peak location in these plots in due to the slight size increase seen in the SuperMan5 cells relative to the BG10 strain shown in the top panels.

Flow cytometry results from plate growth were as expected and showed that the V5 epitope could be expressed on the cell surface of *Pichia* cells constitutively and detected with FITC-labeled antibody, indicating good accessibility of the epitope tag to large protein probes.

Figure 6:
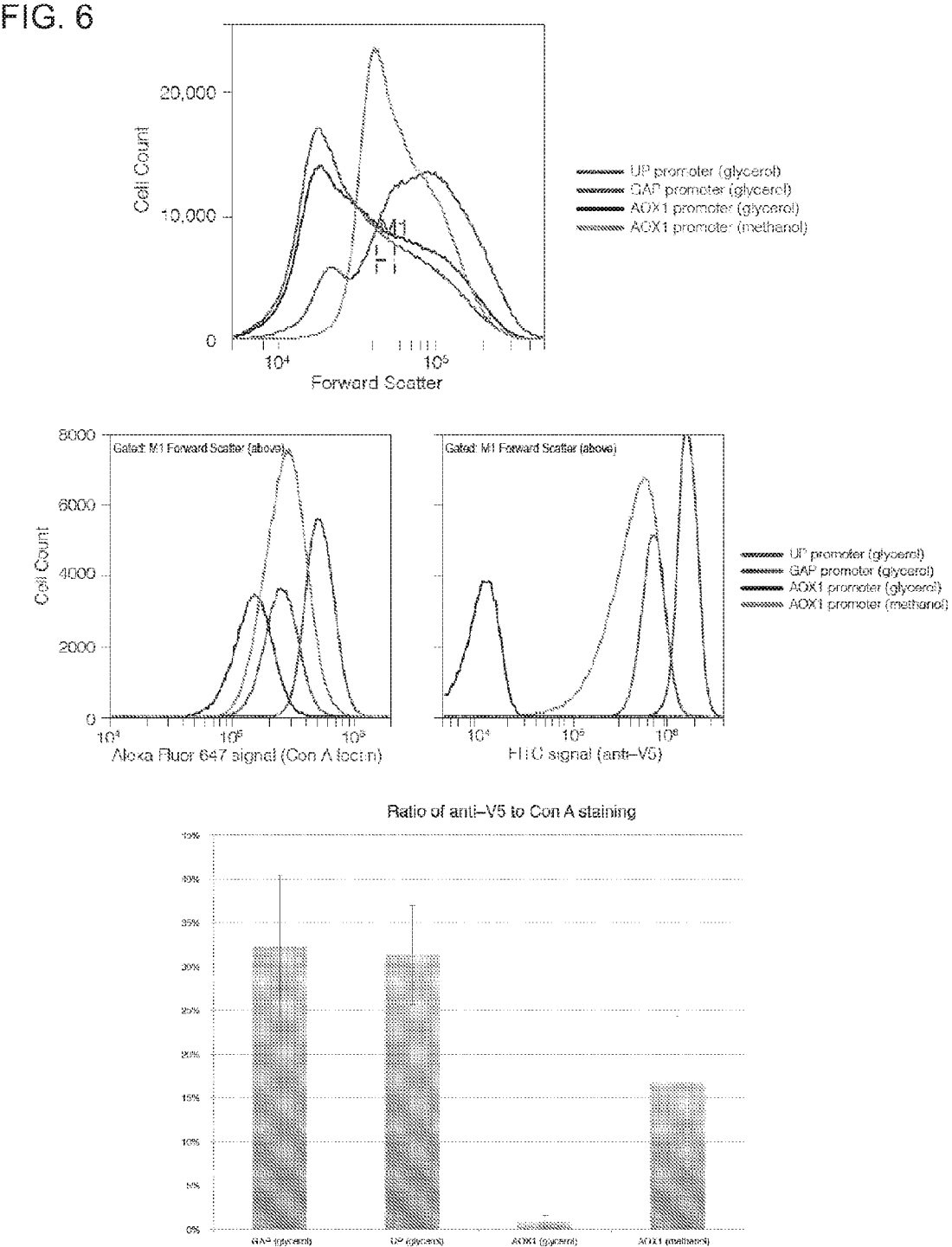
FIG. 6 shows flow cytometry analysis of SuperMan5 cells grown in shake flask culture. AOX1 promoter constructs grown on both glycerol and methanol as the carbon source.

Since all 5 isolates of each transformation looked identical by flow cytometry for plate-grown cells, a single isolate of the AOX1, GAP and UP promoter constructs were picked for shake flask analysis. Cells were grown overnight in synthetic complete medium with glycerol as the carbon source. Cells were spun down and resuspended at a 1/100 dilution in either synthetic complete with glycerol (GAP and UP promoters) or both synthetic complete with glycerol and synthetic complete with methanol (AOX1 promoter). After dilution, cells were grown at 30° C. for 48 h. The methanol culture was supplemented with additional methanol at 24 h. Cells were collected and then blocked and stained as before. Flow cytometry analysis is shown in FIG. 6.

The cells grown in shake flask culture showed a much wider forward scatter distribution than the plate-grown cells. In addition, culture to culture variation in forward scatter was very pronounced, as shown in the first panel of FIG. 6. Much of this heterogeneity appeared (at the microscope level) to be due to differences in cell clumping. In order to compensate for this, a narrow gate of forward scatter (shown as M1 in the first panel) was used to analyze the fluorescence of each culture. As can be seen from the middle set of panels, FITC signal induction was significant for the AOX1 construct. The ratio of ConA to anti-V5 binding is plotted in the bottom panel. The GAP and UP promoter constructs have similar ratios. Even at 48 h, the AOX1 construct has a lower ratio of surface expressed V5.

Aliquots from the same samples that were used for flow cytometry were analyzed by fluorescence microscopy. Even after 48 h of growth, V5 distribution on the surface of the AOX1 constructs was more punctate and heterogeneous than that of the GAP and UP constructs (see FIG. 7, FIG. 8, FIG. 9).

Without wishing to limit the present invention to any theory or mechanism, it is believed that the system of the present invention provides a cell surface display system that allows a binding partner enhanced access to the displayed protein on the engineered *Pichia pastoris* cell surface (as compared to a *S. cerevisiae* and wild type *Pichia pastoris*). Further, as compared to *S. cerevisiae*, the system of the present invention does not require double transformations.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

TABLE 1

SEQ ID NO: 1

| | | | | | |
|---|---|---|---|---|---|
| 1 | AACGTCAAAG | ACAGCAATGG | AGTCAATATT | GATAACACCA | CTGGCAGAGC GGTTCGTACG |
| 61 | TCGTTTTGGA | GCCGATATGA | GGCTCAGCGT | GCTAACAGCA | CGATTGACAA GAAGACTCTC |
| 121 | GAGTGACAGT | AGGTTGAGTA | AAGTATTCGC | TTAGATTCCC | AACCTTCGTT TTATTCTTTC |
| 181 | GTAGACAAAG | AAGCTGCATG | CGAACATAGG | GACAACTTTT | ATAAATCCAA TTGTCAAACC |
| 241 | AACGTAAAAC | CCTCTGGCAC | CATTTTCAAC | ATATATTTGT | GAAGCAGTAC GCAATATCGA |
| 301 | TAAATACTCA | CCGTTGTTTG | TAACAGCCCC | AACTTGCATA | CGCCTTCTAA TGACCTCAAA |
| 361 | TGGATAAGCC | GCAGCTTGTG | CTAACATACC | AGCAGCACCG | CCCGCGGTCA GCTGCGCCCA |
| 421 | CACATATAAA | GGCAATCTAC | GATCATGGGA | GGAATTAGTT | TTGACCGTCA GGTCTTCAAG |
| 431 | AGTTTTGAAC | TCTTCTTCTT | GAACTGTGTA | ACCTTTTAAA | TGACGGGATC TAAATACGTC |
| 541 | ATGGATGAGA | TCATGTGCGT | AAAAACTGAC | TCCAGCATAT | GGAATCATTC CAAAGATTGC |
| 601 | AGGAGCGAAC | CCACGATAAA | AGTTTCCCAA | CCTTGCCAAA | GTGTCTAATG CTGTGACTTG |
| 661 | AAATCTGGGT | TCCTCGTCGA | AGACCCTGCG | TACTATGCCC | AAAAACTTTC CCCCACGAGC |
| 721 | CCTATTAACT | TCTCTATGAG | TTTCAAATGC | CAAACGGACA | CGGATTAGGT CCAATGGGTA |
| 781 | AGTGAAAAAC | ACAGAGCAAA | CCCCAGCTAA | TGAGCCGGCC | AGTAACCGTC TTGGAGCTGT |
| 841 | TTCATAAGAG | TCATTAGGGA | TCAATAACGT | TCTAATCTGT | TCATAACATA CAAATTTTAT |

TABLE 1-continued

```
 901  GGCTGCATAG GGAAAAATTC TCAACAGGGT AGCCGAATGA CCCTGATATA GACCTGCGAC
 961  ACCATCATAC CCATAGATCT GCCTGACAGC CTTAAAGAGC CGCTAAAAG  ACCCGGAAAA
1021  CCGAGAGAAC TCTGGATTAG CAGTCTGAAA AGAATCTTC  ACTCTGTCTA GTGGAGCAAT
1081  TAATGTCTTA GCGGCACTTC CTGCTACTCC GCCAGCTACT CCTGAATAGA TCACATACTG
1141  CAAAGACTGC TTGTCGATGA CCTTGGGGTT ATTTAGCTTC AAGGGCAATT TTTGGGACAT
1201  TTTGGACACA GGAGACTCAG AAACAGACAC AGAGCGTTCT GAGTCCTGGT GCTCCTGACG
1261  TAGGCCTAGA ACAGGAATTA TTGGCTTTAT TTGTTTGTCC ATTTCATAGG CTTGGGGTAA
1321  TAGATAGATG ACAGAGAAAT AGAGAAGACC TAATATTTTT TGTTCATGGC AAATCGCGGG
1381  TTCGCGGTCG GGTCACACAC GGAGAAGTAA TGAGAAGAGC TGGTAATCTG GGGTAAAAGG
1441  GTTCAAAAGA AGGTCGCCTG GTAGGGATGC AATACAAGGT TGTCTTGGAG TTTACATTGA
1501  CCAGATGATT TGGCTTTTTC TCTGTTCAAT TCACATTTTT CAGCGAGAAT CGGATTGACG
1561  GAGAAATGGC GGGGTGTGGG GTGGATAGAT GGCAGAAATG CTCGCAATCA CCGCGAAAGA
1621  AAGACTTTAT GGAATAGAAC TACTGGGTGG TGTAAGGATT ACATAGCTAG TCCAATGGAG
1681  TCCGTTGGAA AGGTAAGAAG AAGCTAAAAC CGGCTAAGTA ACTAGGGAAG AATGATCAGA
1741  CTTTGATTTG ATGAGGTCTG AAAATACTCT GCTGCTTTTT CAGTTGCTTT TTCCCTGCAA
1801  CCTATCATTT TCCTTTTCAT AAGCCTGCCT TTTCTGTTTT CACTTATATG AGTTCCGCCG
1861  AGACTTCCCC AAATTCTCTC CTGGAACATT TCTATCGCT  CTCCTTCCAA GTTGCGCCCC
1921  CTGGCACTGC CTAGTAATAT TACCACGCGA CTTATATTCA GTTCCACAAT TTCCAGTGTT
1981  CGTAGCAAAT ATCATCAGCC TACCGTTCGT ATAGCATACA TTATACGAAC GGTACTTTTT
2041  TGTAGAAATG TCTTGGTGTC CTCGTCCAAT CAGGTAGCCA CCTCTGAAAT ATCTGGCTCC
2101  GTTGCAACTC CGAACGACCT GCTGGCAACG TAAAATTCTC CGGGGTAAAA CTTAAATGTG
2161  GAGTAATGGA ACCAGAAACG TCTCTTCCCT TCTCTCTCCT TCCACCGCCC GTTACCGTCC
2221  CTAGGAAATT TTACTCTGCT GGAGAGCTTC TTCTACGGCC CCCTTGCAGC AATGCTCTTC
2281  CCAGCATTAC GTTGCGGGTA AAACGGAGGT CGTGTACCCG ACCTAGCAGC CCAGGGATGG
2341  AAAAGTCCCG GCCGTCGCTG GCAATAATAG CGGGCGGACG CATGTCATGA GATTATTGGA
2401  AACCACCAGA ATCGAATATA AAAGGCGAAC ACCTTTCCCA ATTTTGGTTT CTCCTGACCC
2461  AAAGACTTTA AATTTAATTT ATTTGTCCCT ATTTCAATCA ATTGAACAAC TATTTCGCGA
2521  AACGATGAGA TTTCCTTCAA TTTTTACTGC TGTTTTATTC GCAGCATCCT CCGCATTAGC
2581  TGCTCCAGTC AACACTACAA CAGAAGATGA AACGGCACAA ATTCCGGCTG AAGCTGTCAT
2641  CGGTTACTCA GATTTAGAAG GGGATTTCGA TGTTGCTGTT TTGCCATTTT CCAACAGCAC
2701  AAATAACGGG TTATTGTTTA TAAATACTAC TATTGCCAGC ATTGCTGCTA AAGAAGAAGG
2761  GGTATCTCTC GAGAAAAGAG AGGCTGAAGC TGAATTCGCC ACAAAACGTG GATCTCCCAA
2821  CCCTACGAGG GCGGCAGCAG TCAAGGCCGC ATTCCAGACG TCGTGGAACG CTTACCACCA
2881  TTTTGCCTTT CCCCATGACG ACCTCCACCC GGTCAGCAAC AGCTTTGATG ATGAGAGAAA
2941  CGGCTGGGGC TCGTCGGCAA TCGATGGCTT GGACACGGCT ATCCTCATGG GGGATGCCGA
3001  CATTGTGAAC ACGATCCTTC AGTATGTACC GCAGATCAAC TTCACCACGA CTGCGGTTGC
3061  CAACCAAGGC ATCTCCGTGT TCGAGACCAA CATTCGGTAC CTCGGTGGCC TGCTTTCTGC
3121  CTATGACCTG TTGCGAGGTC CTTTCAGCTC CTTGGCGACA AACCAGACCC TGGTAAACAG
3181  CCTTCTGAGG CAGGCTCAAA CACTGGCCAA CGGCCTCAAG GTTGCGTTCA CCACTCCCAG
3241  CGGTGTCCCG GACCCTACCG TCTTCTTCAA CCCTACTGTC CGGAGAAGTG GTGCATCTAG
```

TABLE 1-continued

```
3301  CAACAACGTC GCTGAAATTG GAAGCCTGGT GCTCGAGTGG ACACGGTTGA GCGACCTGAC
3361  GGGAAACCCG CAGTATGCCC AGCTTGCGCA GAAGGGCGAG TCGTATCTCC TGAATCCAAA
3421  GGGAAGCCCG GAGGCATGGC CTGGCCTGAT TGGAACGTTT GTCAGCACGA GCAACGGTAC
3481  CTTTCAGGAT AGCAGCGGCA GCTGGTCCGG CCTCATGGAC AGCTTCTACG AGTACCTGAT
3542  CAAGATGTAC CTGTACGACC CGGTTGCGTT TGCACACTAC AAGGATCGCT GGGTCCTTGC
3601  TGCCGACTCG ACCATTGCGC ATCTCGCCTC TCACCCGTCG ACGCGCAAGG ACTTGACCTT
3661  TTTGTCTTCG TACAACGGAC AGTCTACGTC GCCAAACTCA GGACATTTGG CCAGTTTTGC
3721  CGGTGGCAAC TTCATCTTGG GAGGCATTCT CCTGAACGAG CAAAAGTACA TTGACTTTGG
3781  AATCAAGCTT GCCAGCTCGT ACTTTGCCAC GTACAACCAG ACGGCTTCTG GAATCGGCCC
3841  CGAAGGCTTC GCGTGGGTGG ACAGCGTGAC GGGCGCCGGC GGCTCGCCGC CCTCGTCCCA
3901  GTCCGGGTTC TACTCGTCGG CAGGATTCTG GGTGACGGCA CCGTATTACA TCCTGCGGCC
3961  GGAGACGCTG GAGAGCTTGT ACTACGCATA CCGCGTCACG GGCGACTCCA AGTGGCAGGA
4021  CCTGGCGTGG GAAGCGTTCA GTGCCATTGA GGACGCATGC CGCGCCGGCA GCGCGTACTC
4081  GTCCATCAAC GACGTGACGC AGGCCAACGG CGGGGGTGCC TCTGACGATA TGGAGAGCTT
4141  CTGGTTTGCC GAGGCGCTCA AGTATGCGTA CCTGATCTTT GCGGAGGAGT CGGATGTGCA
4201  GGTGCAGGCC AACGGCGGGA ACAAATTTGT CTTTAACACG GAGGCGCACC CCTTTAGCAT
4261  CCGTTCATCA TCACGACGGG GCGGCCACCT TGCTCACGAC GAGTTGTAAT CTAGGGCGGC
4321  CGCCAGCTTG GCCCGAACA AAAACTCATC TCAGAAGAGG ATCTGAATAG CGCCGTCGAC
4381  CATCATCATC ATCATCATTG AGTTTTAGCC TTAGACATGA CTGTTCCTCA GTTCAAGTTG
4441  GGCACTTACG AGAAGACCGG TCTTGCTAGA TTCTAATCAA GAGGATGTCA GAATGCCATT
4501  TGCCTGAGAG ATGCAGGCTT CATTTTTGAT ACTTTTTTAT TTGTAACCTA TATAGTATAG
4561  GATTTTTTTT GTCATTTTGT TTCTTCTCGT ACGAGCTTGC TCCTGATCAG CCTATCTCGC
4621  AGCTGATGAA TATCTTGTGG TAGGGGTTTG GGAAAATCAT TCGAGTTTGA TGTTTTTCTT
4681  GGTATTTCCC ACTCCTCTTC AGAGTACAGA AGATTAAGTG AGACCTTCGT TTGTGCGGAT
4741  CCCCCACACA CCATAGCTTC AAAATGTTTC TACTCCTTTT TTACTCTTCC AGATTTTCTC
4801  GGACTCCGCG CATCGCCGTA CCACTTCAAA ACACCCAAGC ACAGCATACT AAATTTCCCC
4861  TCTTTCTTCC TCTAGGGTGT CGTTAATTAC CCGTACTAAA GGTTTGGAAA AGAAAAAAGA
4921  GACCGCCTCG TTTCTTTTTC TTCGTCGAAA AAGGCAATAA AAATTTTTAT CACGTTTCTT
4981  TTTCTTGAAA ATTTTTTTTT TTGATTTTTT TCTCTTTCGA TGACCTCCCA TTGATATTTA
5041  AGTTAATAAA CGGTCTTCAA TTTCTCAAGT TTCAGTTTCA TTTTTCTTGT TCTATTACAA
5101  CTTTTTTTAC TTCTTGCTCA TTAGAAAGAA AGCATAGCAA TCTAATCTAA GGGCGGTGTT
5161  GACAATTAAT CATCGGCATA GTATATCGGC ATAGTATAAT ACGACAAGGT GAGGAACTAA
5221  ACCATGGCCA AGCCTTTGTC TCAAGAAGAA TCCACCCTCA TTGAAAGAGC AACGGCTACA
5281  ATCAACAGCA TCCCCATCTC TGAAGACTAC AGCGTCGCCA GCGCAGCTCT CTCTAGCGAC
5341  GGCCGCATCT TCACTGGTGT CAATGTATAT CATTTTACTG GGGGACCTTG TGCAGAACTC
5401  GTGGTGCTGG GCACTGCTGC TGCTGCGGCA GCTGGCAACC TGACTTGTAT CGTCGCGATC
5461  GGAAATGAGA ACAGGGGCAT CTTGAGCCCC TGCGGACGGC GCCGACAGGT GCTTCTCGAT
5521  CTGCATCCTG GGATCAAAGC CATAGTGAAG ACAGTGATG ACAGCCGAC GGCAGTTGGG
5581  ATTCGTGAAT TGCTGCCCTC TGGTTATGTG TGGGAGGGCT AAGCACTTCG TGGCCGAGGA
8641  GCAGGACTGA CACGTCCGAC GCGGCCCGAC GGGTCCGAGG CCTCGGAGAT CCGTCCCCCT
```

TABLE 1-continued

```
5701  TTTCCTTTGT CGATATCATG TAATTAGTTA TGTCACGCTT ACATTCACGC CCTCCCCCCA
5761  CATCCGCTCT AACCGAAAAG GAAGGAGTTA GACAACCTGA AGTCTAGGTC CCTATTTATT
5821  TTTTTATAGT TATGTTAGTA TTAAGAACGT TATTTATATT TCAAATTTTT CTTTTTTTTC
5881  TGTACAGACG CGTGTACGCA CGTAACATTA TACTGAAAAC CTTGCTTGAG AAGGTTTTGG
5941  GACGCTCGAA GGCTTTAATT TGCAAGCTGG AGACCAACAT GTGAGCAAAA GGCCAGCAAA
6001  AGGCCAGGAA CCGTAAAAAG GCCGCGTTGC TGGCGTTTTT CCATAGGCTC CGCCCCCCTG
6061  ACGAGCATCA CAAAAATCGA CGCTCAAGTC AGAGGTGGCG AAACCCGACA GGACTATAAA
6121  GATACCAGGC GTTTCCCCCT GGAAGCTCCC TCGTGCGCTC TCCTGTTCCG ACCCTGCCGC
6181  TTACCGGATA CCTGTCCGCC TTTCTCCCTT CGGGAAGCGT GGCGCTTTCT CATAGCTCAC
6241  GCTGTAGGTA TCTCAGTTCG GTGTAGGTCG TTCGCTCCAA GCTGGGCTGT GTGCACGAAC
6301  CCCCCGTTCA GCCCGACCGC TGCGCCTTAT CCGGTAACTA TCGTCTTGAG TCCAACCCGG
6361  TAAGACACGA CTTATCGCCA CTGGCAGCAG CCACTGGTAA CAGGATTAGC AGAGCGAGGT
6421  ATGTAGGCGG TGCTACAGAG TTCTTGAAGT GGTGGCCTAA CTACGGCTAC ACTAGAAGAA
6481  CAGTATTTGG TATCTGCGCT CTGCTGAAGC CAGTTACCTT CGGAAAAAGA GTTGGTAGCT
6541  CTTGATCCGG CAAACAAACC ACCGCTGGTA GCGGTGGTTT TTTTGTTTGC AAGCAGCAGA
6601  TTACGCGCAG AAAAAAAGGA TCTCAAGAAG ATCCTTTGAT CTTTTCTACG GGGTCTGACG
6661  CTCAGTGGAA CGAAAACTCA CGTTAAGGGA TTTTGGTCAT GAGATCAGAT CTAACATCCA
6721  TAATCGTATT CGCCGTTTCT GTCATTTGCG TTTTGTACGG ACCCTCACAA CAATTATCAT
6781  CTCCAAAAAT AGACTATGAT CCATTGACGC TCCGATCACT TGATTTGAAG ACTTTGGAAG
6841  CTCCTTCACA GTTGAGTCCA GGCACCGTAG AAGATAATCT TCGAAGACAA TTGGAGTTTC
6901  ATTTTCCTTA CCGCAGTTAC GAACCTTTTC CCCAACATAT TTGGCAAACG TGGAAAGTTT
6961  CTCCCTCTGA TAGTTCCTTT CCGAAAAACT TCAAAGACTT AGGTGAAAGT TGGCTGCAAA
7021  GGTCCCCAAA TTATGATCAT TTTGTGATAC CCGATGATGC AGCATGGGAA CTTATTCACC
7081  ATGAATACGA ACGTGTACCA GAAGTCTTGG AAGCTTTCCA CCTGCTACCA GAGCCCATTC
7141  TAAAGGCCGA TTTTTTCAGG TATTTGATTC TTTTTGCCCG TGGAGGACTG TATGCTGACA
7201  TGGACACTAT GTTATTAAAA CCAATAGAAT CGTGGCTGAC TTTCAATGAA ACTATTGGTG
7261  GAGTAAAAAA CAATGCTGGG TTGGTCATTG GTATTGAGGC TGATCCTGAT AGACCTGATT
7321  GGCACGACTG GTATGCTAGA AGGATACAAT TTGCCAATG GGCAATTCAG TCCAAACGAG
7381  GACACCCAGC ACTGCGTGAA CTGATTGTAA GAGTTGTCAG CACGACTTTA CGGAAAGAGA
7441  AAAGCGGTTA CTTGAACATG GTGGAAGGAA AGGATCGTGG AAGTGATGTG ATGGACTGGA
7501  CGGGTCCAGG AATATTTACA GACACTCTAT TTGATTATAT GACTAATGTC AATACAACAG
7561  GCCACTCAGG CCAAGGAATT GGAGCTGGCT CAGCGTATTA CAATGCCTTA TCGTTGGAAG
7621  AACGTGATGC CCTCTCTGCC CGCCCGAACG GAGAGATGTT AAAAGAGAAA GTCCCAGGTA
7681  AATATGCACA GCAGGTTGTT TTATGGGAAC AATTTACCAA CCTGCGCTCC CCCAAATTAA
7741  TCGACGATAT TCTTATTCTT CCGATCACCA GCTTCAGTCC AGGGATTGGC CACAGTGGAG
7801  CTGGAGATTT GAACCATCAC CTTGCATATA TTAGGCATAC ATTTGAAGGA AGTTGGAAGG
7861  ACTAAAGAAA GCTAGAGTAA AATAGATATA GCGAGATTAG AGAATGAATA CCTTCTTCTA
7921  AGCGATCGTC CGTCATCATA GAATATCATG GACTGTATAG TTTTTTTTTT GTACATATAA
7981  TGATTAAACG GTCATCCAAC ATCTCGTTGA CAGATCTCTC AGTACGCGAA ATCCCTGACT
8041  ATCAAAGCAA GAACCGATGA AGAAAAAAAC AACAGTAACC CAAACACCAC AACAAACACT
```

TABLE 1-continued

```
8101  TTATCTTCTC CCCCCCAACA CCAATCATCA AAGAGATGTC GGAACCAAAC ACCAAGAAGC
8161  AAAAACTAAC CCCATATAAA AACATCCTGG TAGATAATGC TGGTAACCCG CTCTCCTTCC
8221  ATATTCTGGG CTACTTCACG AAGTCTGACC GGTCTCAGTT GATCAACATG ATCCTCGAAA
8281  TGGGTGGCAA GATCGTTCCA GACCTGCCTC CTCTGGTAGA TGGAGTGTTG TTTTTGACAG
8341  GGGATTACAA GTCTATTGAT GAAGATACCC TAAAGCAACT GGGGGACGTT CCAATATACA
8401  GAGACTCCTT CATCTACCAG TGTTTTGTGC ACAAGACATC TCTTCCCATT GACACTTTCC
8461  GAATTGACAA GAACGTCGAC TTGGCTCAAG ATTTGATCAA TAGGGCCCTT CAAGAGTCTG
8521  TGGATCATGT CACTTCTGCC AGCACAGCTG CAGCTGCTGC TGTTGTTGTC GCTACCAACG
8581  GCCTGTCTTC TAAACCAGAC GCTCGTACTA GCAAAATACA GTTCACTCCC GAAGAAGATC
8641  GTTTTATTCT TGACTTCGTT AGGAGAAATC CTAAACGAAG AAACACACAT CAACTGTACA
8701  CTGAGCTCGC TCAGCACATG AAAAACCATA CGAATCATTC TATCCGCCAC AGATTTCGTC
8761  GTAATCTTTC CGCTCAACTT GATTGGGTTT ATGATATCGA TCCATTGACC AACCAACCTC
8821  GAAAAGATGA AAACGGGAAC TACATCAAGG TACAAGATCT TCCACAAGGA ATTCGTGGTC
8881  ATTATTCTGC CAAGATGAT TACAATTTGT GTTTATCGGT TCAACCTTTC ATTGAATCTG
8941  TAGATGAGAC AACAGGCCAA GAATTTTTCA AACCTCTGAA AGGTGTATTT GATGACTTGG
9001  AATCTCGCTT TCCTCACCAT ACAAAGACTT CCTGGAGAGA CAGATTCAGA AAGTTTGCCT
9061  CTAAATACGG TGTTCGTCAG TACATCGCGT ATTATGAAAA GACTGTTGAA CTCAATGGTG
9121  TTCCTAATCC GATGACGAAC TTTACCTCAA AGGCTTCCAT TGAAAAATTT AGAGAAAGAC
9181  GCGGGACTTC ACGTAACAGT GGCCTTCCAG GCCCGGTTGG TGTAGAAGCT GTAAGCTCTT
9241  TGGACCACAT ATCCCCATTG GTCACATCTA ATTCCAATTC TGCAGCTGCT GCAGCTGCTG
9301  CCGCAGCAGT TGCAGCCTCT GCCTCTGCTT CTTCAGCTCC TAATACTTCA ACTACCAATT
9361  TCTTTGAACA GGAGAATATT GCCCAAGTTC TCTCTGCACA TAACAACGAG CAGTCTATTG
9421  CAGAAGTTAT TGAGTCCGCA CAGAATGTCA ACACCCATGA AAGTGAACCT ATAGCTGATC
9481  ATGTTCGAAA AAATCTTACA GACGATGAAT TGCTTGACAA AATGGATGAT ATTTTAAGCT
9541  CCAGAAGTCT AGGCGGACTA GATGACTTGA TAAAGATCCT CTACACTGAG CTGGGATTTG
9601  CTCATCGTTA TACCGAATTT CTTTTTTACCT CATGTTCTGG TGATGTGATT TTCTTCCGAC
9661  CATTAGTGGA ACATTTCCTT CTTACTGGTG AGTGGAGCT GGAGAATACT CGTGGCATCT
9721  GGACCGGTCG TCAAGACGAA ATGCTACGTG CTAGCAATCT AGATGACCTG CACAAGTTAA
9781  TTGACCTGCA TGGGAAAGAA CGTGTTGAGA CCAGAAGAAA AGCCATCAAG GGAGAATGAT
9841  CATAAGAAAT GAAAACGTA  TAAGT
```

| TABLE 2A |
|---|
| SEQ ID NO: 2 (Wild type OCH1 Protein Sequence) |
| (M)AKADGSLLY YNPHNPPRRY YFYMAIFAVS VICVLYGPSQ |
| QLSSPKIDYD PLTLRSLDLK TLEAPSQLSP GTVEDNLRRQ |
| LEFHFPYRSY EPFPQHIWQT WKVSPSDSSF PKNFKDLGES |
| WLQRSPNYDH FVIPDDAAWE LIHHEYERVP EVLEAFHLLP |
| EPILKADFFR YLILFARGGI YADMDTMLLK PIESWITFNE |
| TIGGVKNNAG LVIGIEADPD RPDWHDWYAR RIQFCQWAIQ |
| SKRGHPALRE LIVRVVSTTL RKEKSGYINM VEGKDRGSDV |

| TABLE 2A-continued |
|---|
| SEQ ID NO: 2 (Wild type OCH1 Protein Sequence) |
| MDWTGPGIFT DTIFDYMTNV NTTGHSGQGI GAGSAYYNAL |
| SLEERDALSA RPNGEMIKEK VPGKYAQQVV LWEQFTNIRS |
| PKLIDDILII PITSFSPGIG HSGAGDLNHH LAYIRHTFEG |
| SWKD |

TABLE 2B

SEQ ID NO: 22 (a mutant OCH1 Protein Sequence)

Met Arg Ser Asp Leu Thr Ser Ile Ile Val Phe Ala
Val Ser Val Ile Cys Val Leu Tyr Gly Pro Ser Gln
Gln Leu Ser Ser Pro Lys Ile Asp Tyr Asp Pro Leu
Thr Leu Arg Ser Leu Asp Leu Lys Thr Leu Glu Ala
Pro Ser Gln Leu Ser Pro Gly Thr Val Glu Asp Asn
Leu Arg Arg Gln Leu Glu Phe His Phe Pro Tyr Arg
Ser Tyr Glu Pro Phe Pro Gln His Ile Trp Gln Thr
Trp Lys Val Ser Pro Ser Asp Ser Ser Phe Pro Lys
Asn Phe Lys Asp Leu Gly Glu Ser Trp Leu Gln Arg
Ser Pro Asn Tyr Asp His Phe Val Ile Pro Asp Asp
Ala Ala Trp Glu Leu Ile His His Glu Tyr Glu Arg
Val Pro Glu Val Leu Glu Ala Phe His Leu Leu Pro
Glu Pro Ile Leu Lys Ala Asp Phe Phe Arg Tyr Leu
Ile Leu Phe Ala Arg Gly Gly Leu Tyr Ala Asp Met
Asp Thr Met Leu Leu Lys Pro Ile Glu Ser Trp Leu
Thr Phe Asn Glu Thr Ile Gly Gly Val Lys Asn Asn
Ala Gly Leu Val Ile Gly Ile Glu Ala Asp Pro Asp
Arg Pro Asp Trp His Asp Trp Tyr Ala Arg Arg Ile
Gln Phe Cys Gln Trp Ala Ile Gln Ser Lys Arg Gly
His Pro Ala Leu Arg Glu Leu Ile Val Arg Val Val
Ser Thr Thr Leu Arg Lys Glu Lys Ser Gly Tyr Leu
Asn Met Val Glu Gly Lys Asp Arg Gly Ser Asp Val
Met Asp Trp Thr Gly Pro Gly Ile Phe Thr Asp Thr
Leu Phe Asp Tyr Met Thr Asn Val Asn Thr Thr Gly
His Ser Gly Gln Gly Ile Gly Ala Gly Ser Ala Tyr
Tyr Asn Ala Leu Ser Leu Glu Glu Arg Asp Ala Leu
Ser Ala Arg Pro Asn Gly Glu Met Leu Lys Glu Lys
Val Pro Gly Lys Tyr Ala Gln Gln Val Val Leu Trp
Glu Gln Phe Thr Asn Leu Arg Ser Pro Lys Leu Ile
Asp Asp Ile Leu Ile Leu Pro Ile Thr Ser Phe Ser
Pro Gly Ile Gly His Ser Gly Ala Gly Asp Leu Asn
His His Leu Ala Tyr Ile Arg His Thr Phe Glu Gly
Ser Trp Lys Asp

TABLE 3 pJGG display sequence (SEQ ID NO: 3)

LOCUS pJGG-display 5475 bp DNA circular UNA

FEATURES        Location/Qualifiers

Promoter        1..558
                /label="GAP promoter"

ORF             559..825
                /label="alpha MF secretion signal"

Restriction_sit 826..849
                /label="BsaI-NotI-BsaI cloning site"

ORF             868..909
                /label="V5 epitope tag"

ORF             910..1872
                /label=Sap1p

PolyA_signal    1873..2222
                /label="AOX1 transcription terminator"

Promoter        2234..2612
                /label="A. gossypii TEF promoter"

ORF             2613..3422
                /note="Length: 810"
                /note="Found at strand: positive"
                /note="Start codon: ATG"
                /label=G418R TABLE 3-continued

| pJGG display sequence (SEQ ID NO: 3) | |
|---|---|
| PolyA_signal | 3423..3659<br>/label="A. gosypii TEF transcription terminator" |
| ORF | complement(4482..5342)<br>/label=AmpR |

ORIGIN
```
   1  CGACTATTAT CGATCAATGA AATCCATCAA GATTGAAATC TTAAAATTGC CCCTTTCACT
  61  TGACAGGATC CTTTTTTGTA GAAATGTCTT GGTGTCCTCG TCCAATCAGG TAGCCATCTC
 121  TGAAATATCT GGCTCCGTTG CAACTCCGAA CGACCTGCTG GCAACGTAAA ATTCTCCGGG
 181  GTAAAACTTA AATGTGGAGT AATGGAACCA GAAACGTCTC TTCCCTTCTC TCTCCTTCCA
 241  CCGCCCGTTA CCGTCCCTAG GAAATTTTAC TCTGCTGGAG AGCTTCTTCT ACGGCCCCCT
 301  TGCAGCAATG CTCTTCCCAG CATTACGTTG CGGGTAAAAC GGAGGTCGTG TACCCGACCT
 361  AGCAGCCCAG GGATGGAAAA GTCCCGGCCG TCGCTGGCAA TAATAGCGGG CGGACGCATG
 421  TCATGAGATT ATTGGAAACC ACCAGAATCG AATATAAAAG GCGAACACCT TTCCCAATTT
 481  TGGTTTCTCC TGACCCAAAG ACTTTAAATT TAATTTATTT GTCCCTATTT CAATCAATTG
 541  AACAACTATC AAAACACGAT GAGATTCCCA TCTATTTTCA CTGCTGTTTT GTTCGCTGCT
 601  TCTTCTGCTT TGGCTGCTCC AGTTAACACT ACTACTGAGG ACGAGACTGC TCAAATTCCA
 661  GCTGAGGCTG TTATTGGTTA CTTGGACTTG GAGGGTGACT TCGACGTTGC TGTTTTGCCA
 721  TTCTCTAACT CTACTAACAA CGGTTTGTTG TTCATTAACA CTACTATTGC TTCTATTGCT
 781  GCTAAGGAGG AGGGTGTTTC TTTGGACAAG AGAGAGGCTG AGGCTCGAGA CCatGCGGCC
 841  GCGGTCTCGG CCGGTGGTGC TTTTGAAGGA AAACCAATTC CAAATCCTTT GTTGGGATTG
 901  GATTCTACTT CTGCCAAATC ATCTTTCATT TCAACCACCA CCACTGATTT GACTTCAATC
 961  AACACTTCTG CTTACTCTAC TGGATCTATT TCAACTGTTG AAACTGGAAA CAGAACCACT
1021  TCTGAAGTTA TTTCTCATGT TGTTACCACT TCCACCAAAC TTTCTCCAAC TGCTACTACT
1081  TCTTTGACCA TTGCTCAAAC TTCAATTTAC TCTACTGATT CCAATATCAC TGTTGGAACT
1141  GATATTCACA CCACTTCTGA AGTTATTTCT GATGTTGAAA CTATTTCAAG AGAAACTGCT
1201  TCTACTGTTG TTGCTGCTCC AACTTCCACC ACTGGATGGA CTGGTGCCAT GAACACTTAT
1261  ATTTCTCAGT TCACTTCTTC TTCTTTTGCC ACTATCAACT CTACTCCAAT CATTTCTTCT
1321  TCTGCTGTTT TTGAAACTTC TGATGCTTCC ATTGTCAATG TTCACACTGA AAATATCACC
1381  AACACTGCTG CTGTTCCATC TGAAGAGCCA ACTTTTGTCA ATGCTACTAG AAACTCTTTG
1441  AACTCTTTTT GTTCTTCCAA ACAACCTTCT TCTCCTTCTT CTTACACTTC TTCTCCTTTG
1501  GTTTCTTCTT TGTCTGTTTC CAAAACTCTT TTGTCAACTT CTTTCACTCC TTCTGTTCCA
1561  ACTTCCAACA CTTATATCAA AACCAAGAAC ACTGGTTATT TTGAACACAC TGCTTTGACC
1621  ACTTCTTCTG TTGGTTTGAA CTCTTTTAGT GAAACTGCTG TTTCTTCTCA AGGAACCAAG
1681  ATTGATACTT TTTTGGTTTC TTCTTTGATT GCTTATCCAT CTTCTGCTTC TGGATCTCAA
1741  TTGTCTGGTA TTCAACAAAA TTTCACTTCC ACTTCTTTGA TGATTTCAAC TTATGAAGGA
1801  AAAGCTTCCA TTTTCTTCTC TGCTGAACTT GGATCTATCA TTTTTTTGTT GTTGAGTTAT
1861  CTTTTGTTTT AATCAAGAGG ATGTCAGAAT GCCATTTGCC TGAGAGATGC AGGCTTCATT
1921  TTTGATACTT TTTTATTTGT AACCTATATA GTATAGGATT TTTTTTGTCA TTTTGTTTCT
1981  TCTCGTACGA GCTTGCTCCT GATCAGCCTA TCTCGCAGCT GATGAATATC TTGTGGTAGG
2041  GGTTTGGGAA AATCATTCGA GTTTGATGTT TTTCTTGGTA TTTCCCACTC CTCTTCAGAG
2101  TACAGAAGAT TAAGTGACAC GTTCGTTTGT GCAAGCTTCA ACGATGCCAA AAGGGTATAA
```

TABLE 3-continued pJGG display sequence (SEQ ID NO: 3)

```
2161  TAAGCGTCAT TTGCAGCATT GTGAAGAAAA CTATGTGGCA AGCCAAGCCT GCGAAGAATG

2221  TAGTCGAGAA TTGAGCTTGC CTCGTCCCCG CCGGGTCACC CGGCCAGCGA CATGGAGGCC

2281  CAGAATACCC TCCTTGACAG TCTTGACGTG CGCAGCTCAG GGGCATGATG TGACTGTCGC

2341  CCGTACATTT AGCCCATACA TCCCCATGTA TAATCATTTG CATCCATACA TTTTGATGGC

2401  CGCACGGCGC GAAGCAAAAA TTACGGCTCC TCGCTGCAGA CCTGCGAGCA GGGAAACGCT

2461  CCCCTCACAG ACGCGTTGAA TTGTCCCCAC GCCGCGCCCC TGTAGAGAAA TATAAAAGGT

2521  TAGGATTTGC CACTGAGGTT CTTCTTTCAT ATACTTCCTT TTAAAATCTT GCTAGGATAC

2581  AGTTCTCACA TCACATCCGA ACATAAACAA AAATGGGTAA GGAAAAGACT CACGTTTCCA

2641  GACCAAGATT GAACTCTAAC ATGGACGCTG ACTTGTACGG TTACAAGTGG GCTAGAGACA

2701  ACGTTGGTCA ATCTGGTGCT ACTATTTACA GATTGTACGG TAAGCCAGAC GCTCCAGAGT

2761  TGTTCTTGAA GCACGGTAAG GGTTCTGTTG CTAACGACGT TACTGACGAG ATGGTTAGAT

2821  TGAACTGGTT GACTGAGTTC ATGCCATTGC CAACTATTAA GCACTTCATT AGAACTCCAG

2881  ACGACGCTTG GTTGTTGACT ACTGCTATTC CAGGTAAGAC TGCTTTCCAA GTTTTGGAGG

2941  AGTACCCAGA CTCTGGTGAG AACATTGTTG ACGCTTTGGC TGTTTTCTTG AGAAGATTGC

3001  ACTCTATTCC AGTTTGTAAC TGTCCATTCA ACTCTGACAG AGTTTTCAGA TTGGCTCAAG

3061  CTCAATCCAG AATGAACAAC GGTTTGGTTG ACGCTTCTGA CTTCGACGAC GAGAGAAACG

3121  GTTGGCCAGT TGAGCAAGTT TGGAAGGAGA TGCACAAGTT GTTGCCATTC TCTCCAGACT

3181  CTGTTGTTAC TCACGGTGAC TTCTCTTTGG ACAACTTGAT TTTCGACGAG GGTAAGTTGA

3241  TTGGTTGTAT TGACGTTGGT AGAGTTGGTA TTGCTGACAG ATACCAAGAC TTGGCTATTT

3301  TGTGGAACTG TTTGGGTGAG TTCTCTCCAT CTTTGCAAAA GAGATTGTTC CAAAAGTACG

3361  GTATTGACAA CCCAGACATG AACAAGTTGC AATTCCACTT GATGTTGGAC GAGTTCTTCT

3421  AAAGTAACTG ACAATAAAAA GATTCTTGTT TTCAAGAACT TGTCATTTGT ATAGTTTTTT

3481  TATATTGTAG TTGTTCTATT TTAATCAAAT GTTAGCGTGA TTTATATTTT TTTTCGCCTC

3541  GACATCATCT GCCCAGATGC GAAGTTAAGT GCGCAGAAAG TAATATCATG CGTCAATCGT

3601  ATGTGAATGC TGGTCGCTAT ACTGCTGTCG ATTCGATACT AACGCCGCCA TCCAGTGTCG

3661  GATCTGTGAG CAAAAGGCCA GCAAAAGGCC AGGAACCGTA AAAAGGCCGC GTTGCTGGCG

3721  TTTTTCCATA GGCTCCGCCC CCCTGACGAG CATCACAAAA ATCGACGCTC AAGTCAGAGG

3781  TGACGAAACC CGACAGGACT ATAAAGATAC CAGGCGTTTC CCCCTGGAAG CTCCCTCGTG

3841  CGCTCTCCTG TTCCGACCCT GCCGCTTACC GGATACCTGT CCGCCTTTCT CCCTTCGGGA

3901  AGCGTGGCGC TTTCTCATAG CTCACGCTGT AGGTATCTCA GTTCGGTGTA GGTCGTTCGC

3961  TCCAAGCTGG GCTGTGTGCA CGAACCCCCC GTTCAGCCCG ACCGCTGCGC CTTATCCGGT

4021  AACTATCGTC TTGAGTCCAA CCCGGTAAGA CACGACTTAT CGCCACTGGC AGCAGCCACT

4081  GGTAACAGGA TTAGCAGAGC GAGGTATGTA GGCGGTGCTA CAGAGTTCTT GAAGTGGTGG

4141  CCTAACTACG GCTACACTAG AAGAACAGTA TTTGGTATCT GCGCTCTGCT GAAGCCAGTT

4201  ACCTTCGGAA AAAGAGTTGG TAGCTCTTGA TCCGGCAAAC AAACCACCGC TGGTAGCGGT

4261  GGTTTTTTTG TTTGCAAGCA GCAGATTACG CGCAGAAAAA AAGGATCTCA AGAAGATCCT

4321  TTGATCTTTT CTACGGGGTC TGACGCTCAG TGGAACGAAA ACTCACGTTA AGGGATTTTG

4381  GTCATGAGAT TATCAAAAAG GATCTTCACC TAGATCCTTT TAAATTAAAA ATGAAGATTT

4441  AAATCAATCT AAAGTATATA TGAGTAAACT TGGTCTGACA GTTACCAATG CTTAATCAGT
```

TABLE 3-continued pJGG display sequence (SEQ ID NO: 3)

```
4501  GAGGCACCTA TCTCAGCGAT CTGTCTATTT CGTTCATCCA TAGTTGCCTG ACTCCCCGTC

4561  GTGTAGATAA CTACGATACG GGAGGGCTTA CCATCTGGCC CCAGTGCTGC AATGATACCG

4621  CGAGATCCAC GCTCACCGGC TCCAGATTTA TCAGCAATAA ACCAGCCGGC GGAAGGGCC

4681  GAGCGCAGAA GTGGGCCGGC CACTTTATCC GCCTCCATCC AGTCTATTAA TTGTTGCCGG

4741  GAAGCTAGAG TAAGTAGTTC GCCAGTTAAT AGTTTGCGCA ACGTTGTTGC CATTGCTACA

4801  GGCATCGTGG TGTCACGCTC GTCGTTTGGT ATGGCTTCAT TCAGCTCCGG TTCCCAACGA

4861  TCAAGGCGAG TTACATGATC CCCCATGTTG TGCAAAAAAG CGGTTAGCTC CTTCGGTCCT

4921  CCGATCGTTG TCAGAAGTAA GTTGGCCGCA GTGTTATCAC TCATGGTTAT GGCAGCACTG

4981  CATAATTCTC TTACTGTCAT GCCATCCGTA AGATGCTTTT CTGTGACTGG TGAGTACTCA

5041  ACCAAGTCAT TCTGAGAATA GTGTATGCGG CGACCGAGTT GCTCTTGCCC GGCGTCAATA

5101  CGGGATAATA CCGCGCCACA TAGCAGAACT TTAAAAGTGC TCATCATTGG AAAACGTTCT

5161  TCGGGGCGAA AACTCTCAAG GATCTTACCG CTGTTGAGAT CCAGTTCGAT GTAACCCACT

5221  CGTGCACCCA ACTGATCTTC AGCATCTTTT ACTTTCACCA GCGTTTCTGG GTGAGCAAAA

5281  ACAGGAAGGC AAAATGCCGC AAAAAAGGGA ATAAGGGCGA CACGGAAATG TTGAATACTC

5341  ATACTCTTCC TTTTTCAATA TTATTGAAGC ATTTATCAGG GTTATTGTCT CATGAGCGGA

5401  TACATATTTG AATGTATTTA GAAAAATAAA CAAATAGGGG TTCCGCGCAC ATTTCCCCGA

5461  AAAGTGCCAC CTGGG
```

TABLE 4 pJAG display sequence (SEQ ID NO: 4)

LOCUS pJAG-display 5855 bp DNA circular UNA

| FEATURES | Location/Qualifiers |
|---|---|
| Promoter | 1..939<br>/label="AOX1 promoter" |
| ORF | 940..1206<br>/label="alpha Mating Factor" |
| Restriction_sit | 1207..1229<br>/label="BsaI-NotI-BsaI cloning site" |
| ORF | 1249..1290<br>/label="V5 eptope tag" |
| ORF | 1291..2253<br>/label=Sag1p |
| PolyA_signal | 2254..2603<br>/label="AOX1 transcription terminator" |
| Promoter | 2615..2993<br>/label="A. gossypii TEF promoter" |
| ORF | 2994..3803<br>/note="Length: 810"<br>/note="Found at strand: positive"<br>/note="Start codon: ATG"<br>/label=G418R |

TABLE 4-continued

| pJAG display sequence (SEQ ID NO: 4) | |
|---|---|
| PolyA_signal | 3804..4040<br>/label="A. gosypii TEF transcription terminator" |
| ORF | complement(4863..5723)<br>/note="Length: 861"<br>/note="Found at strand: negative"<br>/note="Start codon: ATG"<br>/label="beta lactamase" |

```
ORIGIN
    1 GATCTAACAT CCAAAGACGA AAGGTTGAAT GAAACCTTTT TGCCATCCGA CATCCACAGG
   61 TCCATTCTCA CACATAAGTG CCAAACGCAA CAGGAGGGGA TACACTAGCA GCAGACCGTT
  121 GCAAACGCAG GACCTCCACT CCTCTTCTCC TCAACACCCA CTTTTGCCAT CGAAAAACCA
  181 GCCCAGTTAT TGGGCTTGAT TGGAGCTCGC TCATTCCAAT TCCTTCTATT AGGCTACTAA
  241 CACCATGACT TTATTAGCCT GTCTATCCTG GCCCCCCTGG CGAGGTTCAT GTTTGTTTAT
  301 TTCCGAATGC AACAAGCTCC GCATTACACC CGAACATCAC TCCAGATGAG GGCTTTCTGA
  361 GTGTGGGGTC AAATAGTTTC ATGTTCCCCA AATGGCCCAA AACTGACAGT TTAAACGCTG
  421 TCTTGGAACC TAATATGACA AAAGCGTGAT CTCATCCAAG ATGAACTAAG TTTGGTTCGT
  481 TGAAATGCTA ACGGCCAGTT GGTCAAAAAG AAACTTCCAA AAGTCGGCAT ACCGTTTGTC
  541 TTGTTTGGTA TTGATTGACG AATGCTCAAA AATAATCTCA TTAATGCTTA GCGCAGTCTC
  601 TCTATCGCTT CTGAACCCCG GTGCACCTGT GCCGAAACGC AAATGGGGAA ACACCCGCTT
  661 TTTGGATGAT TATGCATTGT CTCCACATTG TATGCTTCCA AGATTCTGGT GGGAATACTG
  721 CTGATAGCCT AACGTTCATG ATCAAAATTT AACTGTTCTA ACCCCTACTT GACAGCAATA
  781 TATAAACAGA AGGAAGCTGC CCTGTCTTAA ACCTTTTTTT TTATCATCAT TATTAGCTTA
  841 CTTTCATAAT TGCGACTGGT TCCAATTGAC AAGCTTTTGA TTTTAACGAC TTTTAACGAC
  901 AACTTGAGAA GATCAAAAAA CAACTAATTA TTCGAAACGA TGAGATTCCC ATCTATTTTC
  961 ACTGCTGTTT TGTTCGCTGC TTCTTCTGCT TTGGCTGCTC CAGTTAACAC TACTACTGAG
 1021 GACGAGACTG CTCAAATTCC AGCTGAGGCT GTTATTGGTT ACTTGGACTT GGAGGGTGAC
 1081 TTCGACGTTG CTGTTTTGCC ATTCTCTAAC TCTACTAACA ACGGTTTGTT GTTCATTAAC
 1141 ACTACTATTG CTTCTATTGC TGCTAAGGAG GAGGGTGTTT CTTTGGACAA GAGAGAGGCT
 1201 GAGGCTCGAG ACCATGCGGC CGCGGTCTCG GCCGGTGGTG CTTTTGAAGG AAAACCAATT
 1261 CCAAATCCTT TGTTGGGATT GGATTCTACT TCTGCCAAAT CATCTTTCAT TTCAACCACC
 1321 ACCACTGATT TGACTTCAAT CAACACTTCT GCTTACTCTA CTGGATCTAT TTCAACTGTT
 1381 GAAACTGGAA ACAGAACCAC TTCTGAAGTT ATTTCTCATG TTGTTACCAC TTCCACCAAA
 1441 CTTTCTCCAA CTGCTACTAC TTCTTTGACC ATTGCTCAAA CTTCAATTTA CTCTACTGAT
 1501 TCCAATATCA CTGTTGGAAC TGATATTCAC ACCACTTCTG AAGTTATTTC TGATGTTGAA
 1561 ACTATTTCAA GAGAAACTGC TTCTACTGTT GTTGCTGCTC AACTTCCAC CACTGGATGG
 1621 ACTGGTGCCA TGAACACTTA TATTTCTCAG TTCACTTCTT CTTCTTTTGC CACTATCAAC
 1681 TCTACTCCAA TCATTTCTTC TTCTGCTGTT TTTGAAACTT CTGATGCTTC CATTGTCAAT
 1741 GTTCACACTG AAAATATCAC CAACACTGCT GCTGTTCCAT CTGAAGAGCC AACTTTTGTC
 1801 AATGCTACTA GAAACTCTTT GAACTCTTTT TGTTCTTCCA ACAACCTTC TTCTCCTTCT
 1861 TCTTACACTT CTTCTCCTTT GGTTTCTTCT TTGTCTGTTT CCAAAACTCT TTTGTCAACT
 1921 TCTTTCACTC CTTCTGTTCC AACTTCCAAC ACTTATATCA AACCAAGAA CACTGGTTAT
 1981 TTGAACACA CTGCTTTGAC CACTTCTTCT GTTGGTTTGA ACTCTTTTAG TGAAACTGCT
```

TABLE 4-continued pJAG display sequence (SEQ ID NO: 4)

| | |
|---|---|
| 2041 | GTTTCTTCTC AAGGAACCAA GATTGATACT TTTTTGGTTT CTTCTTTGAT TGCTTATCCA |
| 2101 | TCTTCTGCTT CTGGATCTCA ATTGTCTGGT ATTCAACAAA ATTTCACTTC CACTTCTTTG |
| 2161 | ATGATTTCAA CTTATGAAGG AAAAGCTTCC ATTTTCTTCT CTGCTGAACT TGGATCTATC |
| 2221 | ATTTTTTTGT TGTTGAGTTA TCTTTTGTTT AATCAAGAG GATGTCAGAA TGCCATTTGC |
| 2281 | CTGAGAGATG CAGGCTTCAT TTTTGATACT TTTTTATTTG TAACCTATAT AGTATAGGAT |
| 2341 | TTTTTTTGTC ATTTTGTTTC TTCTCGTACG AGCTTGCTCC TGATCAGCCT ATCTCGCAGC |
| 2401 | TGATGAATAT CTTGTGGTAG GGGTTTGGGA AAATCATTCG AGTTTGATGT TTTTCTTGGT |
| 2461 | ATTTCCCACT CCTCTTCAGA GTACAGAAGA TTAAGTGACA CGTTCGTTTG TGCAAGCTTC |
| 2521 | AACGATGCCA AAAGGGTATA ATAAGCGTCA TTTGCAGCAT TGTGAAGAAA ACTATGTGGC |
| 2581 | AAGCCAAGCC TGCGAAGAAT GTAGTCGAGA ATTGAGCTTG CCTCGTCCCC GCCGGGTCAC |
| 2641 | CCGGCCAGCG ACATGGAGGC CCAGAATACC CTCCTTGACA GTCTTGACGT GCGCAGCTCA |
| 2701 | GGGGCATGAT GTGACTGTCG CCCGTACATT TAGCCCATAC ATCCCCATGT ATAATCATTT |
| 2761 | GCATCCATAC ATTTTGATGG CCGCACGGCG CGAAGCAAAA ATTACGGCTC CTCGCTGCAG |
| 2821 | ACCTGCGAGC AGGGAAACGC TCCCCTCACA GACGCGTTGA ATTGTCCCCA CGCCGCGCCC |
| 2881 | CTGTAGAGAA ATATAAAAGG TTAGGATTTG CCACTGAGGT TCTTCTTTCA TATACTTCCT |
| 2941 | TTTAAAATCT TGCTAGGATA CAGTTCTCAC ATCACATCCG AACATAAACA AAAATGGGTA |
| 3001 | AGGAAAAGAC TCACGTTTCC AGACCAAGAT TGAACTCTAA CATGGACGCT GACTTGTACG |
| 3061 | GTTACAAGTG GGCTAGAGAC AACGTTGGTC AATCTGGTGC TACTATTTAC AGATTGTACG |
| 3121 | GTAAGCCAGA CGCTCCAGAG TTGTTCTTGA AGCACGGTAA GGGTTCTGTT GCTAACGACG |
| 3181 | TTACTGACGA GATGGTTAGA TTGAACTGGT TGACTGAGTT CATGCCATTG CCAACTATTA |
| 3241 | AGCACTTCAT TAGAACTCCA GACGACGCTT GGTTGTTGAC TACTGCTATT CCAGGTAAGA |
| 3301 | CTGCTTTCCA AGTTTTGGAG GAGTACCCAG ACTCTGGTGA GAACATTGTT GACGCTTTGG |
| 3361 | CTGTTTTCTT GAGAAGATTG CACTCTATTC AGTTTGTAA CTGTCCATTC AACTCTGACA |
| 3421 | GAGTTTTCAG ATTGGCTCAA GCTCAATCCA GAATGAACAA CGGTTTGGTT GACGCTTCTG |
| 3481 | ACTTCGACGA CGAGAGAAAC GGTTGGCCAG TTGAGCAAGT TTGGAAGGAG ATGCACAAGT |
| 3541 | TGTTGCCATT CTCTCCAGAC TCTGTTGTTA CTCACGGTGA CTTCTCTTTG GACAACTTGA |
| 3601 | TTTTCGACGA GGGTAAGTTG ATTGGTTGTA TTGACGTTGG TAGAGTTGGT ATTGCTGACA |
| 3661 | GATACCAAGA CTTGGCTATT TTGTGGAACT GTTTGGGTGA GTTCTCTCCA TCTTTGCAAA |
| 3721 | AGAGATTGTT CCAAAAGTAC GGTATTGACA ACCCAGACAT GAACAAGTTG CAATTCCACT |
| 3781 | TGATGTTGGA CGAGTTCTTC TAAAGTAACT GACAATAAAA AGATTCTTGT TTTCAAGAAC |
| 3841 | TTGTCATTTG TATAGTTTTT TTATATTGTA GTTGTTCTAT TTTAATCAAA TGTTAGCGTG |
| 3901 | ATTTATATTT TTTTTCGCCT CGACATCATC TGCCCAGATG CGAAGTTAAG TGCGCAGAAA |
| 3961 | GTAATATCAT GCGTCAATCG TATGTGAATG CTGGTCGCTA TACTGCTGTC GATTCGATAC |
| 4021 | TAACGCCGCC ATCCAGTGTC GGATCTGTGA GCAAAAGGCC AGCAAAGGC CAGGAACCGT |
| 4081 | AAAAAGGCCG CGTTGCTGGC GTTTTTCCAT AGGCTCCGCC CCCTGACGA GCATCACAAA |
| 4141 | AATCGACGCT CAAGTCAGAG GTGACGAAAC CCGACAGGAC TATAAAGATA CCAGGCGTTT |
| 4201 | CCCCCTGGAA GCTCCCTCGT GCGCTCTCCT GTTCCGACCC TGCCGCTTAC CGGATACCTG |
| 4261 | TCCGCCTTTC TCCCTTCGGG AAGCGTGGCG CTTTCTCATA GCTCACGCTG TAGGTATCTC |
| 4321 | AGTTCGGTGT AGGTCGTTCG CTCCAAGCTG GGCTGTGTGC ACGAACCCCC CGTTCAGCCC |

TABLE 4-continued pJAG display sequence (SEQ ID NO: 4)

```
4381  GACCGCTGCG CCTTATCCGG TAACTATCGT CTTGAGTCCA ACCCGGTAAG ACACGACTTA
4441  TCGCCACTGG CAGCAGCCAC TGGTAACAGG ATTAGCAGAG CGAGGTATGT AGGCGGTGCT
4501  ACAGAGTTCT TGAAGTGGTG GCCTAACTAC GGCTACACTA GAAGAACAGT ATTTGGTATC
4561  TGCGCTCTGC TGAAGCCAGT TACCTTCGGA AAAAGAGTTG GTAGCTCTTG ATCCGGCAAA
4621  CAAACCACCG CTGGTAGCGG TGGTTTTTTT GTTTGCAAGC AGCAGATTAC GCGCAGAAAA
4681  AAAGGATCTC AAGAAGATCC TTTGATCTTT TCTACGGGGT CTGACGCTCA GTGGAACGAA
4741  AACTCACGTT AAGGGATTTT GGTCATGAGA TTATCAAAAA GGATCTTCAC CTAGATCCTT
4801  TTTAATTAAA AATGAAGATT TAAATCAATC TAAAGTATAT ATGAGTAAAC TTGGTCTGAC
4861  AGTTACCAAT GCTTAATCAG TGAGGCACCT ATCTCAGCGA TCTGTCTATT TCGTTCATCC
4921  ATAGTTGCCT GACTCCCCGT CGTGTAGATA ACTACGATAC GGGAGGGCTT ACCATCTGGC
4981  CCCAGTGCTG CAATGATACC GCGAGATCCA CGCTCACCGG CTCCAGATTT ATCAGCAATA
5041  AACCAGCCGG CCGGAAGGGC CGAGCGCAGA AGTGGGCCGG CCACTTTATC CGCCTCCATC
5101  CAGTCTATTA ATTGTTGCCG GGAAGCTAGA GTAAGTAGTT CGCCAGTTAA TAGTTTGCGC
5161  AACGTTGTTG CCATTGCTAC AGGCATCGTG GTGTCACGCT CGTCGTTTGG TATGGCTTCA
5221  TTCAGCTCCG GTTCCCAACG ATCAAGGCGA GTTACATGAT CCCCCATGTT GTGCAAAAAA
5281  GCGGTTAGCT CCTTCGGTCC TCCGATCGTT GTCAGAAGTA AGTTGGCCGC AGTGTTATCA
5341  CTCATGGTTA TGGCAGCACT GCATAATTCT CTTACTGTCA TGCCATCCGT AAGATGCTTT
5401  TCTGTGACTG GTGAGTACTC AACCAAGTCA TTCTGAGAAT AGTGTATGCG GCGACCGAGT
5461  TGCTCTTGCC CGGCGTCAAT ACGGGATAAT ACCGCGCCAC ATAGCAGAAC TTTAAAAGTG
5521  CTCATCATTG GAAAACGTTC TTCGGGGCGA AAACTCTCAA GGATCTTACC GCTGTTGAGA
5581  TCCAGTTCGA TGTAACCCAC TCGTGCACCC AACTGATCTT CAGCATCTTT TACTTTCACC
5641  AGCGTTTCTG GGTGAGCAAA AACAGGAAGG CAAAATGCCG CAAAAAAGGG AATAAGGGCG
5701  ACACGGAAAT GTTGAATACT CATACTCTTC CTTTTTCAAT ATTATTGAAG CATTTATCAG
5761  GGTTATTGTC TCATGAGCGG ATACATATTT GAATGTATTT AGAAAAATAA ACAAATAGGG
5821  GTTCCGCGCA CATTTCCCCG AAAAGTGCCA CCTGG
//
```

TABLE 5 pJUG UP promoter, SEQ ID NO: 5)

GGGTGAAAGCCAACCATCTTTGTTTCGGGGAACCGTGCTCGCCCCGTAAA

GTTAATTTTTTTTTCCCGCGCAGCTTTAATCTTTCGGCAGAGAAGGCGTT

TTCATCGTAGCGTGGGAACAGAATAATCAGTTCATGTGCTATACAGGCAC

ATGGCAGCAGTCACTATTTTGCTTTTTAACCTTAAAGTCGTTCATCAATC

ATTAACTGACCAATCAGATTTTTTGCATTTGCCACTTATCTAAAAATACT

TTTGTATCTCGCAGATACGTTCAGTGGTTTCCAGGACAACACCCAAAAAA

AGGTATCAATGCCACTAGGCAGTCGGTTTTATTTTTGGTCACCCACGCAA

AGAAGCACCCACCTCTTTTAGGTTTTAAGTTGTGGGAACAGTAACACCGC

CTAGAGCTTCAGGAAAAACCAGTACCTGTGACCGCAATTCACCATGATGC

AGAATGTTAATTTAAACGAGTGCCAAATCAAGATTTCAACAGACAAATCA

TABLE 5-continued pJUG UP promoter, SEQ ID NO: 5)

ATCGATCCATAGTTACCCATTCCAGCCTTTTCGTCGTCGAGCCTGCTTCA

TTCCTGCCTCAGGTGCATAACTTTGCATGAAAAGTCCAGATTAGGGCAGA

TTTTGAGTTTAAAATAGGAAATATAAACAAATATACCGCGAAAAAGGTTT

GTTTATAGCTTTTCGCCTGGTGCCGTACGGTATAAATACATACTCTCCTC

CCCCCCCTGGTTCTCTTTTTCTTTTGTTACTTACATTTTACCGTTCCGTC

ACTCGCTTCACTCAACAACAAAA

What is claimed is:

1. A surface display system comprising:
   (a) an engineered strain of *Pichia pastoris* comprising a mutant α-1,6-mannosyltransferase (OCH1) allele which is transcribed into a mRNA coding for a mutant OCH1 protein, wherein the mutant OCH1 protein comprises a catalytic domain at least 95% identical with amino acids 45-404 of SEQ ID NO: 2, wherein the mutant OCH1 protein lacks an N-terminal sequence for targeting the mutant OCH1 protein to the Golgi apparatus and lacks a membrane anchor domain at the N-terminal region, and wherein said strain produce substantially homogeneous N-glycans; and
   (b) a vector encoding a recombinant protein adapted to be displayed on a surface of the *Pichia pastoris*.

2. The system of claim 1, wherein the lack of a membrane anchor domain in the mutant OCH1 protein is a result of deletion of an N-terminal portion of the OCH1 wild type protein.

3. The system of claim 2, wherein the deletion portion further comprises one or more amino acids of the cytoplasmic tail of the wild type OCH1 protein.

4. The system of claim 1, wherein said mutant OCH1 protein comprises the sequence as set forth in SEQ ID NO: 22.

5. The system of claim 1, wherein said strain further comprises a nucleic acid coding for and expressing an a-1,2-mannosidase or a functional fragment thereof.

6. The system of claim 5, wherein said nucleic acid coding for and expressing said a-1,2-mannosidase or said functional fragment thereof is integrated at the OCH1 locus of the strain.

7. The system of claim 6, wherein the OCH1 locus comprises the nucleotide sequence as set forth in SEQ ID NO: 1.

8. The system of claim 5, wherein said strain produces substantially homogeneous N-glycans with Man5GlcNAc2 being the predominant N-glycan form.

9. The system of claim 1, further comprising a nucleic acid coding for and expressing a recombinant protein.

10. The system of claim 1, wherein the system is provided in a kit, wherein the vector comprises SEQ ID NO: 3 or SEQ ID NO: 4 or SEQ ID NO:5, and the vector is adapted to be inserted into the *Pichia pastoris* strain.

11. A method of displaying a recombinant protein, said method comprising:
   (a) providing a system according to claim 1;
   (b) introducing the vector of said system into the engineered strain of said system; and
   (c) subjecting the strain to a protein expression protocol.

12. The method of claim 11, wherein the protein expression protocol comprises methanol induction.

* * * * *